United States Patent
Scuderi, Jr. et al.

(10) Patent No.: US 8,231,869 B2
(45) Date of Patent: Jul. 31, 2012

(54) RECOMBINANT PLASMIN FOR OPTHALMIC INDICATIONS

(75) Inventors: Philip Scuderi, Jr., Chapel Hill, NC (US); Vikram Arora, Morrisville, NC (US); Jennifer A. Hunt, Raleigh, NC (US); Valery Novokhatny, Raleigh, NC (US); Stephen R. Petteway, Jr., Cary, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 604 days.

(21) Appl. No.: 12/090,782

(22) PCT Filed: Oct. 18, 2006

(86) PCT No.: PCT/US2006/040940
§ 371 (c)(1),
(2), (4) Date: Mar. 23, 2009

(87) PCT Pub. No.: WO2007/047874
PCT Pub. Date: Apr. 26, 2007

(65) Prior Publication Data
US 2010/0047228 A1 Feb. 25, 2010

Related U.S. Application Data

(60) Provisional application No. 60/732,588, filed on Nov. 2, 2005, provisional application No. 60/728,615, filed on Oct. 20, 2005.

(51) Int. Cl.
*A61K 38/48* (2006.01)
(52) U.S. Cl. .................................... 424/94.64
(58) Field of Classification Search ........................ None
See application file for complete search history.

(56) References Cited

U.S. PATENT DOCUMENTS

| 2003/0147877 A1 | 8/2003 | Trese et al. |
| 2005/0118158 A1 | 6/2005 | Pakola et al. |
| 2010/0304465 A1* | 12/2010 | Hunt et al. ............... 435/219 |

FOREIGN PATENT DOCUMENTS

| WO | WO 2004052228 | * | 6/2004 |
| WO | WO 2005105990 | * | 11/2005 |

OTHER PUBLICATIONS

Sottrup-Jensen et al, Amino-acid sequence of activation cleavage site in plasminogen: homology with "pro" part of prothrombin. Proc Natl Acad Sci U S A. Jul. 1975;72(7):2577-81.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Unal et al,The efficacy of plasminogen-urokinase combination in inducing posterior vitreous detachment. Retina. 2000;20(1):69-75.*
Walther et al, Activation of human plasminogen by urokinase. Partial characterization of a pre-activation peptide. J Biol Chem. Feb. 25, 1974;249(4):1173-81.*
Wu et al, A fast-acting, modular-structured staphylokinase fusion with Kringle-1 from human plasminogen as the fibrin-targeting domain offers improved clot lysis efficacy. J Biol Chem. May 16, 2003;278(20):18199-206. Epub Mar. 19, 2003.*
Bhisitkul, Robert B., "Anticipation for enzymatic vitreolysis," *Br. J. Ophthalmol.*, 85: 1-3 (2001).
Gandorfer, A., et al., "Ultrastructure of the viteoretinal interface following plasmin assisted vitrectomy," *Br. J. Ophthalmol.*, 85: 6-10 (2001).
Gandorfer, A., et al., "Posterior Vitreous Detachment Induced by Microplasmin," *IOVS*, 45(2): 641-641 (2004).
Li, X, et al., "Posterior vitreous detachment with plasmin in the isolated human eye," *Graefe's Arch. Clin, Exp. Ophthalmol.*, 240: 56-62 (2002).
Trese, Michael T., "Enzymatic Vitreous Surgery," *Seminars in Ophthalmology*, 15(2): 116-121 (2000).
Verstraeten, T.C., et al., "Pharmacologic Induction of Posterior Vitreous Detachment in the Rabbit," *Arch Ophthalmol*, 111: 849-854 (1993).
Wang, Z-L, et al., "PVD Following Plasmin But Not Hyaluronidase: Implications for Combination Pharmacologic Vitreolysis Therapy," *Retina*, 25: 38-43 (2005).
Wang, F., et al., "Safety and Efficacy of Displase and Plasmin in Pharmacologic Vitreolysis," *IOVS*, 45(9): 3286-3290 (2004).
Williams, J.G., et al., "Autologous Plasmin Enzyme in the Surgical Management of Diabetic Retinopathy," *Ophthalmology* 108(10): 1902-1905 (2001).
Anonick, P., et al., "Regulation of Plasmin, Miniplasmin and Streptokinase-Plasmin Complex by $\alpha_2$-Antiplasmin, $\alpha_2$-Macroglobulin, and Antithrombin III in the Presence of Heparin," *Thrombosis Res.*, 59: 449-462 (1990).
Bennett, D., et al., "Kinetic Characterization of the Interaction of Biotinylated Human Interleukin 5 with an Fc Chimera of its Receptor $\alpha$ Subunit and Development of an ELISA Screening Assay using Real-Time Interaction Biosensor Analysis," *J. Molecular Recognition*, 8: 52-58 (1995).
Bowie, J.U., et al., "Deciphering the Message in Protein Sequences: Tolerance to Amino Acid Substitutions," *Science*, 247: 1306-1310 (1990).
Castellino, F.J., and S.G. McCance, "The kringle domains of human plasminogen," *Ciba Found. Symp.*, 212: 46-65 (1997).
Chang, Y., et al., "Structure and Ligand Binding Determinants of the Recombinant Kringle 5 Domain of Human Plasminogen," *Biochemistry*, 37: 3258-3271 (1998).

(Continued)

*Primary Examiner* — Sheridan Swope
(74) *Attorney, Agent, or Firm* — Womble Carlyle Sandridge & Rice, LLP

(57) ABSTRACT

Methods of using polynucleotides and polypeptides relating to a recombinantly-modified plasmin(ogen) molecule are provided, including methods related to vitrectomy or vitreolysis. The plasmin(ogen) molecule has a single kringel domain N-terminal to the activation site present in the native human plasminogen molecule, and exhibits lysine-binding and significant enzymatic characteristics associated with the native enzyme.

22 Claims, 13 Drawing Sheets

OTHER PUBLICATIONS

Chase, T. and E. Shaw, "Titration of Trypsin, Plasmin, and Thrombin with p-Nitrophenyl p'-Guanidinobenzoate HCl," *Methods Enzymol.*, 19: 20-27 (1970).

Cunningham, B.C., and J.A. Wells, "High-Resolution Epitope Mapping of hGH-Receptor Interactions by Alanine-Scanning Mutagenesis," *Science*, 244: 1081-1085 (1989).

de Vos, A.M., et al., "Human Growth Hormone and Extracellular Domain of its Receptor: Crystal Structure of the Complex," *Science*, 255: 306-312 (1992).

Douglas, J.T., et al., "The Two-Domain NK1 Fragment of Plasminogen: Flding, Ligand Binding, and Thermal Stability Profile," *Biochemistry*, 41(10): 3302-3310 (2002).

Houghten, R.A., "General method for the rapid solid-phase synthesis of large numbers of peptides: Specificity of antigen-antibody interaction at the level of individual amino acids," *Proc. Natl. Acad. Sci. USA*, 82: 5131-5135 (1985).

Gribskov, M., and Richard R. Burgess, "Sigma factors from *E. coli, B. subtilis*, phage SP01, and phage T4 are homologous proteins," *Nucl. Acids Res.*, 14(6): 6745-6763 (1986).

Hoover, G.J., et al., "Amino Acids of the Recombinant Kringle 1 Domain of Human Plasminogen that Stabilize its Interaction with ω-Amino Acids," *Biochemistry*, 32(41): 10936-10943 (1993).

Johanson, K., et al., "Binding Interactions of Human Interleukin 5 with its Receptor α Subunit," *J. Biol. Chem.*, 270(16): 9459-9471 (1995).

Lee, H., et al., "Disruption of Interkringle Disulfide Bond of Plasminogen Kringle 1-3 Changes the Lysine Binding Capability of Kringle 2, But Not its Antiangiogenic Activity," *Arch. Biochem. Biophys.*, 375(2): 359-363 (2000).

Lerch, P.G., et al., "Localization of Individual Lysine-Binding Regions in Human Plasminogen and Investigations on Their Complex-Forming Properties," *Eur. J. Biochem.*, 107(1): 7-13 (1980).

Lucas, M.A., et al., "The Binding of Human Plasminogen to Fibrin and Fibrinogen," *J. Biol. Chem.*, 258(7): 42497-4256 (1983).

McCance, S., et al., "Amino Acid Residues of the Kringle-4 and Kringle-5 Domains of Human Plasminogen that Stabilize their Interactions with ω-Amino Acid Ligands," *J. Biol. Chem.*, 269(51): 32405-32410 (1994).

Marder, V.J., et al., "Plasmin Induces Local Thrombolysis without Causing Hemorrhage: A Comparison with Tissue Plasminogen Activator in the Rabbit," *Thromb. Haemost.*, 86(3): 739-745 (2001).

Matsuka, Y.V., et al., "Fluorescence spectroscopic analysis of ligand binding to kringle 1+2+3 and kringle 1 fragments from human plasminogen," *Eur. J. Biochem.*, 190: 93-97 (1990).

Menhart, N., et al., "Functional Independence of the Kringle 4 and Kringle 5 Regions of Human Plasminogen," *Biochemistry*, 32: 8799-8806 (1993).

Motta, A., et al., "Complete Assignment of the Aromatic Proton Magnetic Resonance Spectrum of the Kringle 1 Domain from Human Plasminogen: Structure of the Ligand-Binding Site," *Biochemistry*, 26(13): 3827-3836 (1987).

Novokhatny, V., et al., "Thrombolytic potency of acid-stabilized plasmin: superiority over tissue-type plasminogen activator in an in vitro model of catheter-assisted thrombolysis," *J. Thromb. Haemost.*, 1(5): 1034-1041 (2003).

Novokhatny, V., and Stanislav A. Kudinov, "Domains in Human Plasminogen," *J. Mol. Biol.*, 179: 215-232 (1984).

Novokhatny, V., et al., "Analysis of Ligand Binding to Kringles 4 and 5 Fragments from Human Plasminogen," *Thromb Res.*, 53(3): 243-52 (1989).

Rejante, M.R. and M. Llinas, "Solution structure of the ε-aminohexanoic acid complex of human plasminogen kringle 1," *Eur. J. Biochem.*, 221(3): 939-949 (1994).

Smith, L.J., et al., "Human Interleukin 4: The Solution Structure of a Four-helix Bundle Protein," *J. Mol. Biol.*, 224: 899-904 (1992).

Sottrup-Jensen, L., et al., "The Primary Structure of Human Plasminogen: Isolation of Two Lysine-Binding Fragments and One "Mini-" Plasminogen (MW, 38,000) by Elastase-Catalyzed-Specific Limited Proteolysis," *Prog. Chem. Fibrinol. Thrombol.*, 3: 191-209 (1978).

Thewes, T., et al., "Ligand Interactions with the Kringle 5 Domain of Plasminogen," *J. Biol. Chem.*, 265(7): 3906-3915 (1990).

Wiman, B. and Désiré Collen, *Nature*, 272: 549-550 (1978).

Wiman, B. and Désiré Collen, "On the Kinetics of the Reaction between Human Antiplasmin and Plasmin," *Eur. J. Biochem.*, 84: 573-578 (1978).

Wiman, B., et al., "On the Specific Interaction Between the Lysine-Binding Sites in Plasmin and Complementary Sites in $\alpha_2$-Antiplasmin and in Fibrinogen," *Biochim. Biophys. Acta*, 579: 142-154 (1979).

Wohl, R.C., et al., "Kinetics of Activation of Human Plasminogen by Different Activator Species at pH 7.4 and 37° C.," *J. Biol. Chem.* 255(5): 2005-2013 (1980).

Wohl, R.C., et al., "Steady State Kinetics of Activation of Human and Bovine Plasminogens by Streptokinase and Its Equimolar Complexes with Various Activated Forms of Human Plasminogen," *J. Biol. Chem.*, 253(5): 1402-1407 (1978).

Wu, T.P., et al., "The structure of recombinant plasminogen kringle 1 and the fibrin binding site," *Blood Coagul. Fibrinolysis*, 5(2): 157-166 (1994).

Zajicek, J., et al., "The Effects of Ligand Binding on the Backbone Dynamics of the Kringle 1 Domain of Human Plasminogen," *J. Mol. Biol.*, 301(2): 333-347 (2000).

International Search Report (PCT/US2006/040940; filed: Oct. 18, 2006).

*Journal of Thrombosis and Haemostasis* 2005; 3(1): Abstract No. P0781, Hunt et al.

* cited by examiner

FIG. 3

-19                   1
MEHKEVVLLLLLFLKSGQGEPLDDYVNTQGASLFSVTKKQLGAGSIEECAAKCEEDEEFTCRAFQ

78
YHSKEQQCVIMAENRKSSIIIRMRDVVLFEKKVYLSECKTGNGKNYRGTMSKTKNGITCQKWSST 136    143       153      162
SPHRPRFSPATHPSEGLEENYCRNPDNDPQGPWCYTTDPEKRYDYCDILECEEECMHCSGENYDG
        kringle 1

KISKTMSGLECQAWDSQSPHAHGYIPSKFPNKNLKKNYCRNPDRELRPWCFTTDPNKRWELCDIP
             kringle 2

RCTTPPPSSGPTYQCLKGTGENYRGNVAVTVSGHTCQHWSAQTPHTHNRTPENFPCKNLDENYCR
                                                        kringle 3

NPDGKRAPWCHTTNSQVRWEYCKIPSCDSSPVSTEQLAPTAPPELTPVVQDCYHGDGQSYRGTSS

TTTTGKKCQSWSSMTPHRHQKTPENYPNAGLTMNYCRNPDADKGPWCFTTDPSVRWEYCNLKKCS
              kringle 4

GTEASVVAPPPVVLLPDVETPSEEDCMFGNGKGYRGKRATTVTGTPCQDWAAQEPHRHSIFTPET
                                                           kringle 5

542
NPRAGLEKNYCRNPDGDVGGPWCYTTNPRKLYDYCDVPQCAAPSFDCGKPQVEPKKCPGRVVGGC

VAHPHSWPWQVSLRTRFGMHFCGGTLISPEWVLTAAHCLEKSPRPSSYKVILGAHQEVNLEPHVQ

EIEVSRLFLEPTRKDIALLKLSSPAVITDKVIPACLPSPNYVVADRTECFITGWGETQGTFGAGL

LKEAQLPVIENKVCNRYEFLNGRVQSTELCAGHLAGGTDSCQGDSGGPLVCFEKDKYILQGVTSW

791
GLGCARPNKPGVYVRVSRFVTWIEGVMRNN        (SEQ ID NO:4)

FIG. 4

```
HK1    CKTGNGKNYR  GTMSKTKNGI  TCQKWSSTSP  HR-PRFSPAT  HPSEGLEENY
HK2    CMHCSGENYD  GKISKTMSGL  ECQAWDSQSP  HA-HGYIPSK  FPNKNLKKNY
HK3    CLKGTGENYR  GNVAVTVSGH  TCQHWSAQTP  HT-HNRTPEN  FPCKNLDENY
HK4    CYHGDGQSYR  GTSSTTTTGK  KCQSWSSMTP  HR-HQKTPEN  YPNAGLTMNY
HK5    CMFGNGKGYR  GKRATTVTGT  PCQDWAAQEP  HRHSIFTPET  NPRAGLEKNY (con't)
HK1    CRNPDNDPQG  PWCYTTDPEK  RYDYCDILEC  (SEQ ID NO:5)
HK2    CRNPDRE-LR  PWCFTTDPNK  RWELCDIPRC  (SEQ ID NO:6)
HK3    CRNPDGK-RA  PWCHTTNSQV  RWEYCKIPSC  (SEQ ID NO:7)
HK4    CRNPDAD-KG  PWCFTTDPSV  RWEYCNLKKC  (SEQ ID NO:8)
HK5    CRNPDGDVGG  PWCYTTNPRK  LYDYCDVPQC  (SEQ ID NO:9)
```

FIG. 5

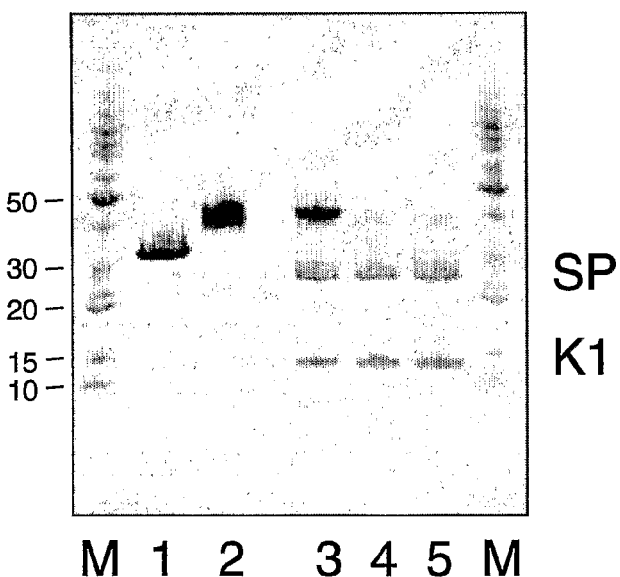

Plasmin:
Km 193 +/- 7 µM
$k_{cat}$: 760 min$^{-1}$

Mini-plasmin:
Km 160 +/- 30 µM
$k_{cat}$: 770 min$^{-1}$

Micro-plasmin:
Km 145 +/- 13 µM
$k_{cat}$: 795 min$^{-1}$

Delta-plasmin:
Km 138 +/- 5 µM
$k_{cat}$: 755 min$^{-1}$

Percent of posterior vitreous detachment vs. time (Mean ± standard deviation)

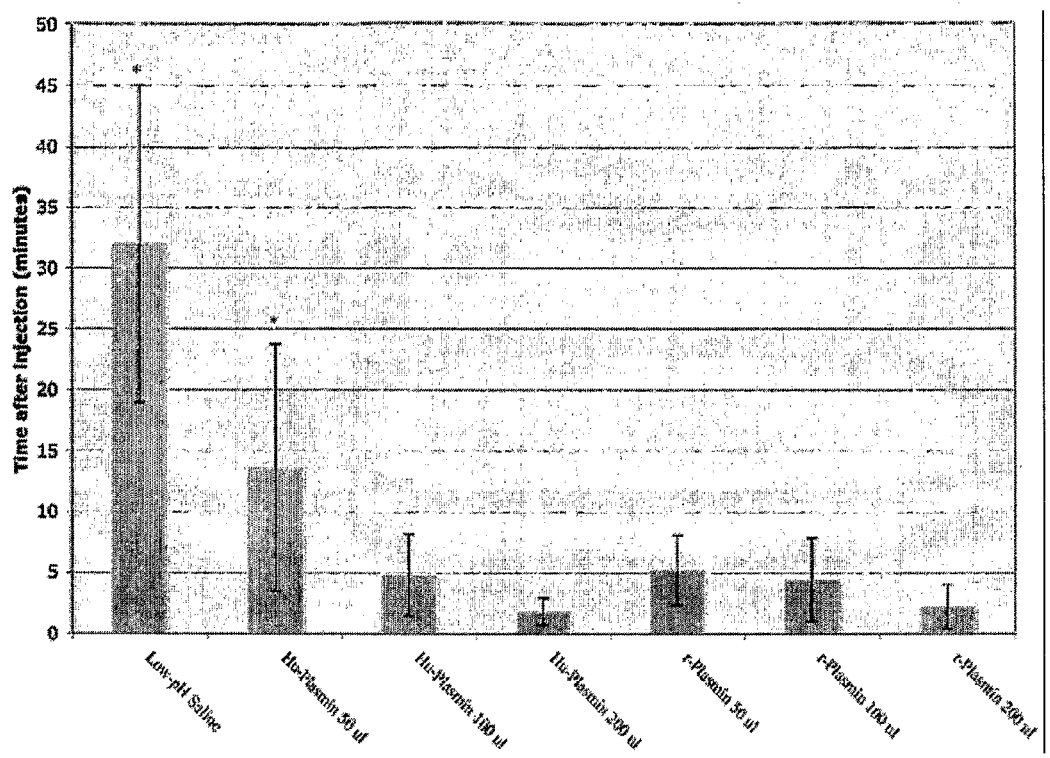
FIG. 16 -Time from injection to signs of initial PVD (Mean ± standard deviation)

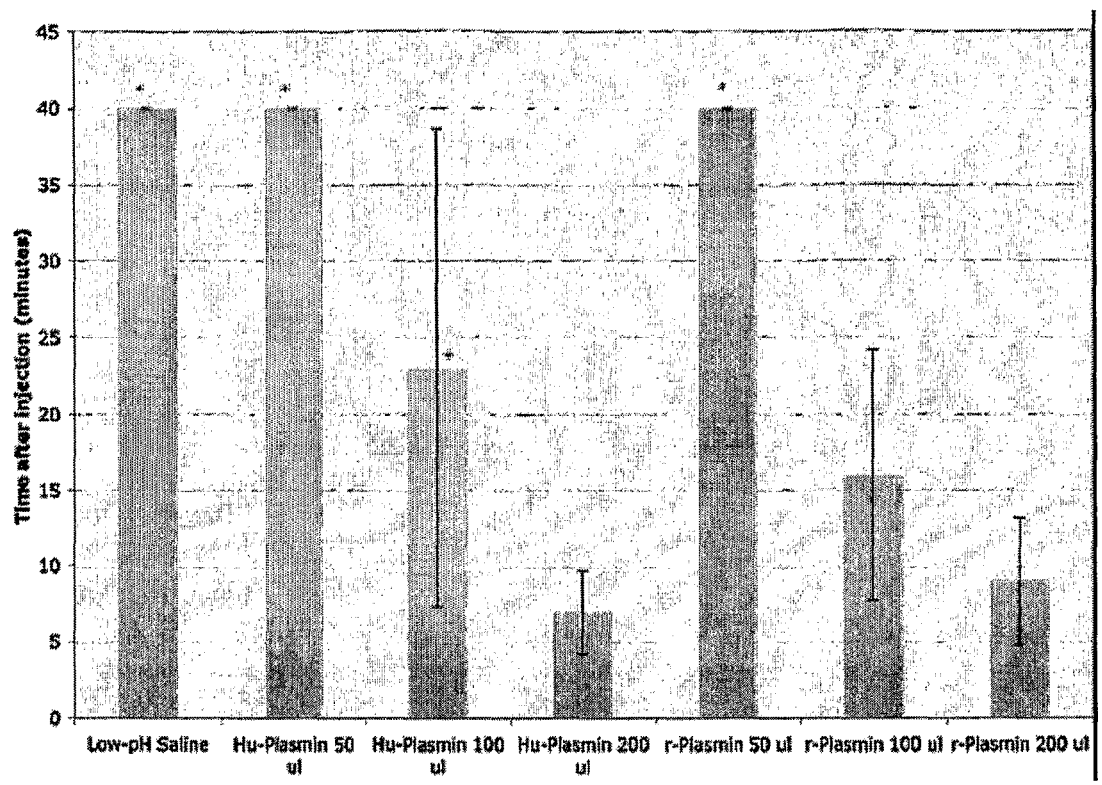
FIG. 17 - Time from injection to 100% PVD

US 8,231,869 B2

RECOMBINANT PLASMIN FOR OPTHALMIC INDICATIONS

RELATED APPLICATIONS

The present application is a National Phase Application under §371 of International Application Serial Number PCT/US06/40940 filed on Oct. 18, 2006, which claims benefit of priority to Provisional Application Ser. No. 60/732,588, filed on Nov. 2, 2005, and Provisional Application Ser. No. 60/728,615, filed on Oct. 20, 2005, the contents of each are herein incorporated by reference in their entirety.

BACKGROUND OF THE INVENTION

Human plasminogen is a single-chain protein containing 791 amino acid residues. Activation of plasminogen to plasmin results from a single cleavage of the Arg561-Val562 peptide bond in the zymogen. The resulting plasmin molecule is a two-chain, disulfide-linked serine protease with trypsin-like specificity (cleaves after Lys and Arg).

The amino-terminal heavy chain of plasmin (residues 1-561, ~60 kDa) is composed of five kringle domains, each containing approximately 80 amino acid residues. The kringle domains are responsible for the regulatory properties of plasminogen, such as interaction with activation inhibitors, e.g., $Cl^{-1}$ ions; with activation stimulators, e.g., ε-aminocaproic acid; with mammalian and bacterial cells; and with other proteins, such as plasmin physiological substrate fibrin and plasmin inhibitor α2-antiplasmin. Of all five kringles, kringle 1 is one of the most multi-functional: its lysine-binding activity has been shown to be responsible for plasmin interaction with α2-antiplasmin and fibrin. See Wiman, B., et al., *Biochim. Biophys. Acta* 579:142-154 (1979); and Lucas, M. A., et al., *J. Biol. Chem.* 258:4249-4256 (1983).

The C-terminal light chain of plasmin (residues 562-791, ~25 kDa) is a typical serine protease, homologous to trypsin and containing the classic serine protease catalytic triad: His603, Asp646 and Ser741. Plasminogen contains 24 disulfide bridges and 2 glycosylation sites, on Asn289 and Thr346.

The limited proteolysis of plasminogen by elastase has been shown to result in three fragments (Sottrup-Jensen, L., et al., *Prog. Chem. Fibrinol. Thrombol.*, 3:191-209 (1978)). First fragment, K1-3, includes the first three kringles and can be isolated in two versions, Tyr79-Val338 and Tyr79-Val354. The second fragment, K4, corresponds to the fourth kringle and includes residues Val355-Ala440. The last, C-terminal fragment (the so-called mini-plasminogen) includes residues Val443-Asn791 and consists of the fifth kringle and the serine protease domain. Mini-plasminogen can be activated in the same way as plasminogen, forming mini-plasmin.

Because of the complex structure of the full-length plasminogen molecule, bacterial expression systems have not proven useful for recombinant plasminogen production. Plasminogen is produced in the form of insoluble inclusion bodies and is not re-foldable from that state. Further, the expression of plasminogen in mammalian cells is complicated by intracellular activation of plasminogen into plasmin and the resulting cytotoxicity. Production of fully active plasminogen using insect cells is possible, however, this system is not suitable for large-scale production due to low yield.

Accordingly, a modified recombinant protein, possessing the desirable characteristics of plasmin/plasminogen while lacking certain negative characteristics and being capable of production in bacterial cells in substantial quantities, is desirable.

SUMMARY OF THE INVENTION

The present invention provides a polynucleotide comprising a nucleotide sequence encoding a polypeptide having a single N-terminal kringle domain homologous to a kringle domain of native human plasminogen; and a C-terminal domain activation site and serine protease domain homologous to the corresponding domains in human plasminogen; wherein the polypeptide binds to immobilized lysine. The N-terminal kringle domain can be homologous to kringle 1 or kringle 4 of native human plasminogen.

In some embodiments, the encoded polypeptide is at least 90%, 95%, or 98% identical to the sequence shown in SEQ ID NO:2. Further, the encoded polypeptide can be the sequence shown in SEQ ID NO:2.

The nucleotide sequence of the polynucleotide can be the sequence shown in SEQ ID NO:1 or degenerate variations thereof. The nucleotide sequence can encode a polypeptide having an N-terminal kringle domain homologous to the kringle 1 or kringle 4 domain of native human plasminogen; and a C-terminal domain activation site and serine protease domain homologous to the corresponding domains in human plasminogen. The nucleotide sequence can also encode a polypeptide having a single N-terminal kringle domain at least 90% identical to the kringle 1 or kringle 4 domain of native human plasminogen; and a C-terminal domain at least 90% identical to the activation site and serine protease domain of human plasminogen. The encoded polypeptides can bind immobilized lysine.

In another aspect, the invention provides polypeptides having an N-terminal kringle domain homologous to a kringle domain of native human plasminogen; and a C-terminal domain activation site and serine protease domain homologous to the corresponding domains in human plasminogen.

In some embodiments, the polypeptides can have an N-terminal kringle domain homologous to kringle 1 or kringle 4 of native human plasminogen.

In some embodiments, the polypeptides can exhibit a fibrinolytic activity that is inhibited by $\alpha_2$-antiplasmin at a rate that is at least about 5-fold faster than the rate of inhibition of the fibrinolytic activity of mini-plasmin by $\alpha_2$-antiplasmin. The rate of inhibition by $\alpha_2$-antiplasmin can also be at least about 10-fold, 20-fold, 30-fold, or 40-fold faster than the rate of inhibition of mini-plasmin.

In some embodiments, the polypeptides can bind immobilized lysine. The immobilized lysine can be lysine bound to a solid support matrix selected from the group consisting of lysine-agarose, lysine-BIOGEL (BioRad, Hercules, Calif.), lysine-HYPERD (Pall Life Sciences, East Hills, N.Y., a lysine-hydrogel), lysine-SEPHAROSE (SEPHAROSE is cross-linked agarose). The immobilized lysine can be lysine-SEPHAROSE.

In some embodiments, the polypeptides can exhibit a lower binding affinity for fibrinogen than the binding affinity for fibrinogen of mini-plasmin.

In some embodiments, the polypeptides can exhibit higher binding affinity for partially cleaved fibrin than the binding affinity for partially cleaved fibrin of mini-plasmin.

In some embodiments, the polypeptides can have a single kringle domain located N-terminal to a plasminogen activation site and plasminogen serine protease domain, wherein the kringle domain has at least one residue greater amino acid sequence identity with kringle 1 or kringle 4 of native human plasminogen than with kringle 5 of native human plasminogen. For these embodiments, it will be understood that conservative substitutions of the kringle regions of the polypeptides of the invention, relative to the native sequences of kringles 1 and 4 of human plasminogen, would not be considered as differing from the native sequences for purposes of the identity comparison with kringle 5.

In some embodiments, the polypeptides can have the amino acid sequence as shown in SEQ ID NO:2, and conservative substitutions thereof The polypeptides can have a residue at a relative position analogous to that of position 76 of the amino acid sequence shown in SEQ ID NO:2 that is arginine.

In another aspect, the invention includes vectors comprising the polynucleotides of the invention, and cultured host cells comprising the vectors.

In yet another aspect, the invention relates to therapeutic or preventative methods of treating eyes of human or animal subjects, i.e., ophthalmic use.

Accordingly, the invention includes a method of liquefying a vitreous and/or inducing posterior vitreous detachment of an eye of a subject, comprising contacting the vitreous and/or an aqueous humor in the eye of the subject with an effective amount of a composition comprising delta-plasmin, wherein the method results in liquefying a vitreous and/or inducing posterior vitreous detachment of the eye of a subject. In some embodiments, the composition is a liquid solution, wherein the step of contacting the vitreous and/or the aqueous humor with the composition comprises injecting the liquid solution into the vitreous and/or the aqueous humor. The effective amount of delta-plasmin can be in the range of 0.005 mg to 1 mg.

The method can be used for treating a subject having, or at risk of developing, a vitreoretinal disease or disorder. The method can also be used to prevent a subject from developing a vitreoretinal disease or disorder.

The method can performed in the absence of vitrectomy or can be performed as an adjunct to vitrectomy.

The invention also includes, in one aspect, a method of treating or preventing a vitreoretinal disease or disorder, or a complication of a vitreoretinal disease or disorder, of an eye of a subject, comprising contacting a vitreous and/or an aqueous humor in the eye of the subject with an effective amount of a composition comprising delta-plasmin, wherein the method results in vitreous liquefaction and/or posterior vitreous detachment in the eye of the subject, thereby treating or preventing the vitreoretinal disease or disorder, or a complication of the vitreoretinal disease or disorder, of the eye of the subject. The composition can be a liquid solution, and the step of contacting the vitreous and/or the aqueous humor with the composition can comprise injecting the liquid solution into the vitreous and/or the aqueous humor. The method can performed in the absence of vitrectomy or as an adjunct to vitrectomy. The effective amount of delta-plasmin can be in the range of 0.005 mg to 1 mg.

The invention also includes, in one aspect, a method of performing a vitrectomy in a subject, comprising contacting a vitreous and/or aqueous humor of an eye of the subject with an effective amount of a composition comprising delta-plasmin, prior to or at the same time as the removal of the vitreous. The composition can be a liquid solution, and the step of contacting the vitreous and/or the aqueous humor with the composition can comprise injecting the liquid solution into the vitreous and/or the aqueous humor. The effective amount of delta-plasmin can be in the range of 0.005 mg to 1 mg.

BRIEF DESCRIPTION OF THE DRAWINGS

FIG. 3 shows the amino acid sequence of native human plasminogen, showing the 19-residue leader sequence numbered as −19 to −1, and the plasminogen sequence shown as residues 1-791; see SEQ ID NO: 3 (cDNA sequence for native human plasminogen; and SEQ ID NO: 4, the encoded amino acid sequence for native human plasminogen, as shown in FIG. 3). A number of features are shown, including the following: the delta-plasminogen sequence (shaded); kringle domains 1-5 (double underscore); glycosylations sites Asn289 and Thr346 (in bold); the plasminogen Arg580-Val581 activation site (in bold); and lysine-binding sites in kringle 1 (in underscore and with specific position numbering).

FIG. 4 shows polypeptide sequence comparisons between the five kringle domains (1-5) of native human plasmin(ogen). Amino acid residues that are identical to those of the same relative position in kringle 1 are shown in underscore.

FIG. 5 shows a 8-25% gradient SDS-PAGE of a non-reduced (Lane 1) and reduced (Lane 2) delta-plasminogen preparation. Activation of delta-plasminogen into delta-plasmin with streptokinase (Lane 3), tissue Plasminogen Activator (tPA) (Lane 4), and urokinase (Lane 5) results in the formation of the two-chain molecule consisting of kringle 1 (K1) and the serine protease domain (SP) connected by two disulfide bridges.

FIG. 16 shows a graphic representation of the time from injection to signs of initial PVD for eyes injected with the indicated volumes of h-plasmin, r-plasmin, or saline.

FIG. 17 shows a graphic representation of the time from injection to 100% PVD for eyes injected with the indicated volumes of h-plasmin, r-plasmin, or saline.

DESCRIPTION OF THE INVENTION

Figure 1:
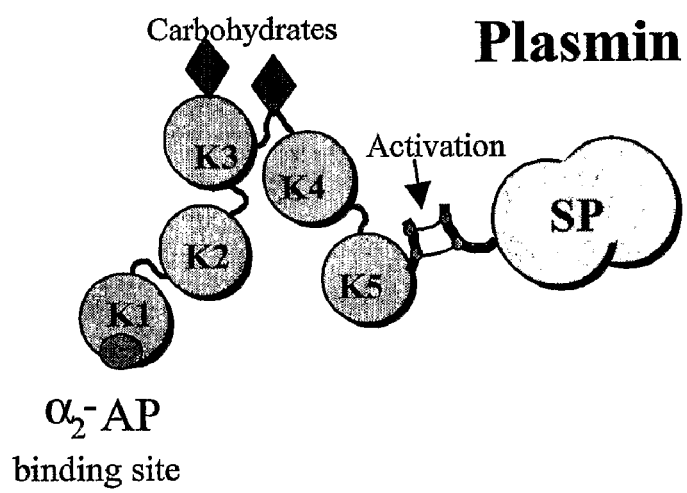
FIG. 1 is a schematic representation of native plasmin after activation by proteolytic cleavage. K1-K5 are kringle regions 1-5; and SP is the serine protease domain. "α2-AP" is the $\alpha_2$-antiplasmin binding site on kringle 1.
Figure 2:
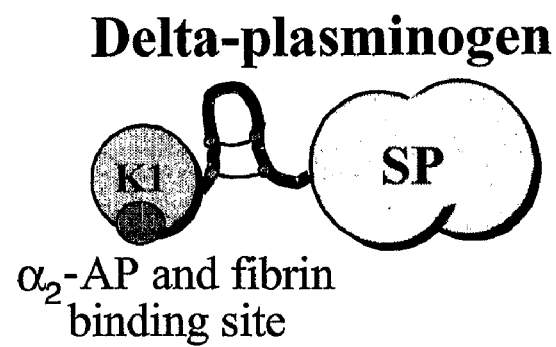
FIG. 2 is a schematic representation of a plasminogen deletion mutant of the invention using the same nomenclature as in FIG. 1, and showing the deletion of K2-5.

In order to provide a simple, non-glycosylated molecule having the fibrin- and antiplasmin-binding properties of full-length plasmin, the present invention provides a deletion mutant of plasminogen. In this mutant, referred to herein as delta-plasminogen, at least a portion of the native amino acid sequence between a domain homologous to kringle 1 and the activation site is deleted. In one aspect, the domain homologous to the native kringle 1 domain of human plasminogen can be directly attached to the serine protease portion of plasminogen, or an homologous, functional analog thereof, with substantially only the intervening native sequence containing the plasminogen activation site remaining between the domains.

Delta-plasmin(ogen) according to the present invention can be characterized by: lower molecular weight (37,198 Da) of delta-plasmin can result in increased specific activity (per mg of protein); the lack of at least two glycosylation sites found in the native protein (see FIG. 3), combined with the relatively low molecular weight, can facilitate recombinant production of this protein using relatively inexpensive bacterial and yeast expression systems; delta-plasminogen can be activated by plasminogen activators tPA, urokinase, and streptokinase; the presence of the domain homologous to native kringle 1 preserves the fibrin-binding properties of plasmin which can be important for thrombolytic efficacy; presence of α2-antiplasmin-binding sites on the domain homologous to kringle 1 can allow delta-plasmin to be inhibited rapidly by this physiological inhibitor of plasmin (a feature which can prevent bleeding); the smaller size of delta-plasmin can facilitate its inhibition by $\alpha_2$-macroglobulin, further lessening the chance of bleeding complications relative to native plasmin. In particular embodiments, the absence of kringle 5, which retains the primary binding site for intact, undigested fibrin(ogen), can allow use of delta-plasmin with reduced depletion of circulating fibrinogen.

Generally, the invention provides recombinant plasmin(ogen) molecules having a single kringle region N-terminal to the activation site and serine protease domain, having certain advantages relative to mini-plasmin(ogen). Although the delta-plasminogen polypeptides of the invention only have one kringle region, as such, N-terminal to the activation site, some embodiments include additional sequences N-terminal to the activation site. Additional N-terminal sequences can be derived from those of native kringle regions of plasminogen.

The N-terminal kringle domains of the present invention include kringle sequences of kringles 1 and 4 of native plasmin(ogen) and functional equivalents thereof. In particular, see the discussion below which provides guidance regarding preservation of function in polypeptide variants, including preservation of residues participating in or influencing lysine-binding.

DEFINITIONS

The terms "domain" and "region" of a polypeptide are generally synonymous as used herein, unless otherwise indicated to the contrary. When recited together with well-recognized structural or functional designations such as "kringle" or "serine protease," etc., such terms will introduce a polypeptide feature relating to at least some characteristic(s) commonly recognized and understood to be associated with the polypeptide structures corresponding to such designations.

A "cultured host cell," as used herein, refers to a prokaryotic or eukaryotic cell that contains heterologous DNA that has been introduced into the cell by any means, e.g., electroporation, calcium phosphate precipitation, microinjection, transformation, viral infection, and the like.

"Heterologous" as used herein means "of different natural origin" or representing a non-natural state. For example, if a cultured host cell is transformed with a DNA or gene derived from another organism, particularly from another species, that gene is heterologous with respect to that cultured host cell and also with respect to descendants of the cultured host cell which carry that gene. Similarly, "heterologous" refers to a nucleotide sequence derived from and inserted into the same natural, original cell type, but which is present in a non-natural state, e.g., a different copy number or under the control of different regulatory elements.

A "vector" molecule is a nucleic acid molecule into which heterologous nucleic acid can be inserted which can then be introduced into an appropriate cultured host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes."

As used herein, the term "transcriptional control sequence" refers to nucleic acid sequences, such as initiator sequences, enhancer sequences and promoter sequences, which induce, repress, or otherwise control the transcription of protein encoding nucleic acid sequences to which they are operably-linked.

The term "polypeptide" is used interchangeably herein with the terms "peptide" and "protein."

The terms "polynucleotide" and "nucleic acid" are used interchangeably herein, and can refer to any nucleic acid that contains the information necessary for the purpose indicated by the context. That is, the nucleic acid can be DNA or RNA, either single stranded or double stranded, or other nucleic acid, as long as the polymer is capable of representing the appropriate information, e.g., in relation to an encoded peptide, and can include complementary sequences, e.g., sense strands and anti-sense strands of nucleic acids polymers.

The term "variant" of a polypeptide refers to an amino acid sequence that is altered by one or more amino acids. The variant can have "conservative" changes, wherein a substituted amino acid has similar structural or chemical properties, e.g., replacement of leucine with isoleucine. Alternatively, a variant can have "non-conservative" changes, e.g., replacement of a glycine with a tryptophan. Analogous minor variation can also include amino acid deletion or insertion, or both. A particular form of a "variant" polypeptide is a "functionally equivalent" polypeptide, i.e., a polypeptide which exhibits substantially similar in vivo or in vitro activity as the examples of the polypeptide of invention, as described in more detail below. Guidance in determining which amino acid residues can be substituted, inserted, or deleted without eliminating biological or immunological activity can be found using computer programs well-known in the art, for example, DNASTAR software (DNASTAR, Inc., Madison, Wis.). Further, specific guidance is provided below, including that provided within the cited references which are fully incorporated herein by reference.

The terms "N-terminal" and "C-terminal" are used herein to designate the relative position of any amino acid sequence or polypeptide domain or structure to which they are applied. The relative positioning will be apparent from the context. That is, an "N-terminal" feature will be located at least closer to the N-terminus of the polypeptide molecule than another feature discussed in the same context (the other feature possible referred to as "C-terminal" to the first feature). Similarly, the terms "5'-" and "3'-" can be used herein to designate relative positions of features of polynucleotides.

The delta-plasminogen/plasmin polypeptides referred to herein as having a N-terminal domain "homologous to a kringle domain of native human plasminogen" exhibit structural and functional characteristics similar to native kringle domains of plasminogen. Further, the delta-plasminogen/plasmin polypeptides referred to herein as having a N-terminal domain "homologous to kringle 1" exhibit characteristics similar to native kringle 1, at least to the extent that the polypeptides can have a higher affinity for ω-aminocarboxylic acids (and functional homologs such as trans-4-aminomethylcyclohexane-1-carboxylic acid, a cyclic acid) than kringle 5. See, e.g., Chang, Y., et al., *Biochemistry* 37:3258-3271 (1998), incorporated herein by reference, for conditions and protocols for comparison of binding of isolated kringle domain polypeptides to 5-aminopentanoic acid (5-APnA); 6-aminohexanoic acid (6-AHxA), also known as ε-aminocaprioic acid (sACA); 7-aminoheptanoic acid (7-AHpA); and trans-4-aminomethylcyclohexane-1-carboxylic acid (t-AMCHA).

References to kringle domains "homologous to kringle 4" are defined similarly, as noted above regarding the phrase "homologous to kringle 1." That is; they exhibit functional characteristics similar to kringle 1 of native human plasminogen as discussed above. These polypeptides also bind immobilized lysine as described above.

The polypeptides of the invention bind immobilized lysine. As used herein, the phrase "binding immobilized lysine" means that the polypeptides so characterized are retarded in their progress relative to mini-plasminogen when subjected to column chromatography using lysine-SEPHAROSE as the chromatographic media. Typically, the polypeptides of the invention can be eluted from such chromatographic media (lysine affinity resins) using solutions containing the specific ligand, e.g., εACA, as eluants.

Further, in addition to Chang et al., supra, other references can be consulted by those of skill in the art to determine which residues can be varied by conservative or non-conservative substitution, deletion or addition to yield a deletion mutant within the scope of the present invention. For example, the following references provide information regarding particular residues of the native kringle domains that may be important for binding of ω aminocarboxylic acids: U.S. Pat. No. 6,538,103 to Ji, et al.; U.S. Pat. No. 6,218,517 to Suzuki; Douglas, J. T., et al., *Biochemistry* 41(10):3302-10 (2002); Zajicek, J., et al., *J. Mol. Biol.*, 301(2):333-47 (2000); Lee H., et al., *Arch Biochem Biophys.*, 375(2):359-63 (2000); Castellino, F. and S. McCance, *Ciba Found Symp.* 212:46-60 (1997); McCance, S., et al., J. Biol. Chem., 269:32405-32410 (1994); Rejante, M. R. and M. Llinas, *Eur. J. Biochem.*, 221 (3):939-49 (1994); Wu, T. P., et al., *Blood Coagul. Fibrinolysis,* 5(2):157-66 (1994); Hoover, C. J., et al., *Biochemistry,* 32(41):10936-43 (1993); Menhart, N., et al., *Biochemistry,* 32:8799-8806 (1993); Thewes, T., et al., *J. Biol. Chem.,* 265 (7):3906-3915 (1990); Novokhatny, V., et al., *Thromb Res.,* 53(3):243-52 (1989); Motta, A., et al., *Biochemistry,* 26(13): 3827-36 (1987); Novokhatny, V., et al., *J. Mol. Biol.,* 179:215-232 (1984); Lerch, P. G., et al., *Eur. J. Biochem.,* 107(1):7-13 (1980); Sottrup-Jensen, L., et al., *Prog. Chem. Fibrinol. Thrombol.,* 3:191-209 (1978); and Wiman, B. and D. Collen, *Nature* 272, 549-545 (1978), all incorporated herein by reference in their entirety.

Because the present inventors have recognized that a valuable, simplified plasmin(ogen) molecule can be prepared having an N-terminal kringle domain having advantageous functional characteristics (which can be evaluated, in part, by testing for the binding of immobilized lysine as described herein), the present invention can encompass other fibrin-binding domains or regions N-terminal to the activation site. For example, the invention can include polypeptides in which the serine protease domain of plasmin is attached to a fibrin-binding kringle selected from a group including, but not limited to, kringle 4 of human plasminogen, kringle 2 of tPA, or a kringle of apolipoprotein (a). Further, the invention can include polypeptides in which a serine protease domain of plasmin is attached to any other known fibrin-binding modules, such as the "finger" domain of tPA or fibronectin, or the FAB fragment of fibrin-specific IgG.

In particular embodiments, residues at certain positions of the N-terminal kringle domain of delta-plasminogen are conserved relative to kringle 1 of native human plasminogen. These can be residues at positions associated with lysine binding, and include Pro136-Pro140, Pro143-Tyr146, and Arg153-Tyr156 (positions numbered as shown in FIG. 3). Some embodiments of the delta-plasminogen of the invention can have Arg at position 153. In other embodiments, the specific positions of the named residues can vary somewhat while still being present in the polypeptide at structurally and functionally analogous positions (i.e. relative to the kringle structure of the N-terminal domain; see Chang, Y., et al. as discussed above). In some embodiments, the N-terminal kringle region of the delta-plasmin(ogen) polypeptide has at least one residue greater percent identity with kringle 1 or kringle 4 of native human plasminogen than with kringle 5 of native human plasminogen.

Additionally, particular embodiments of the invention can be characterized functionally by contrast to mini-plasmin (ogen) which has a similar domain composition, i.e., kringle-serine protease (K-SP) (see Sottrup-Jensen, L., et al., Progress in Chemical Fibrinolysis and Thrombolysis, Vol. 3, (Eds: J. F. Davidson, et al.) Raven Press, New York (1978)). In preferred embodiments, the delta-plasmin of the invention exhibits an increased rate of inhibition by $\alpha_2$-antiplasmin, e.g., as much as about one or two orders of magnitude faster than the rate of inhibition of mini-plasmin. Further, in particular embodiments, delta-plasmin binds immobilized lysine (e.g., lysine-SEPHAROSE).

Characterization of the kringle domain of delta-plasminogen as "N-terminal" means only that the domain is present N-terminal to the activation site and does not mean that additional amino acids residues N-terminal to the domain itself are not present. Further, the number and identity of residues interposed between the domain homologous to kringle 1 and the activation site of plasminogen can be varied without departing from the scope of the present invention. One of skill in the art will be able to determine these variations that achieve the benefits of the invention (kringle 1-like binding of ω aminocarboxylic acids, without substantial increase in size of the deletion mutant or introduction of potentially problematic glycosylation sites) without undue experimentation based on the disclosure herein and the references cited herein for guidance regarding kringle 1 function and structure.

As used herein, "treating" or "treatment" means or implies the reduction or amelioration of any medical disorder to any extent, and includes, but does not require, a complete cure of the disorder. Similarly, the terms "preventing" or "prevention" mean or imply defending or protecting against the development of a disorder or reducing the development or further development thereof, i.e., to function as a prophylactic, at least to some degree.

Accordingly, the invention relates to polynucleotides, polypeptides, recombinant methods for producing the polypeptides, vectors containing the polynucleotides, expression systems for producing the polypeptides, and cultured host cells comprising such expression systems.

As noted, in one aspect, the invention relates to a polynucleotide encoding the polypeptide disclosed herein or a polypeptide having conservative amino acid substitutions thereof. Guidance regarding selection of "conservative" amino acid substitutions is provide in more detail below. In one embodiment, the polynucleotide is DNA.

In another aspect, the invention relates to a method of making a vector comprising inserting the polynucleotide of the invention into a vector. In another aspect, the invention relates to a vector produced by the method of the invention.

In another aspect, the invention relates to a method of making a cultured host cell comprising introducing the vector of the invention into a cultured host cell. In another aspect, the invention relates to a cultured host cell produced by the method of the invention.

In another aspect, the invention relates to an isolated polypeptide of the invention, produced by a method comprising: (a) introducing a vector comprising a polynucleotide encoding the polypeptide into a cultured host cell; (b) culturing the host cell; and (c) recovering the polypeptide. In another aspect, the invention relates to a method for producing a polypeptide comprising: (a) culturing the host cell of the invention under conditions that the vector is expressed; and (b) recovering the polypeptide.

In another aspect, the invention relates to cells containing at least one polynucleotide of the invention.

In one embodiment, the polynucleotide comprises the nucleotide sequence as shown in SEQ ID NO:1. In another embodiment, the polypeptide comprises the amino acid sequence as shown in SEQ ID NO:2.

Polynucleotides

The polynucleotides of the invention include variants which have substitutions, deletions, and/or additions which can involve one or more nucleotides. The variants can be altered in coding regions, non-coding regions, or both. Alterations in the coding regions can produce conservative or non-conservative amino acid substitutions, deletions or additions. Especially preferred among these are silent substitutions, additions and deletions, which do not alter the properties and activities of the delta-plasmin(ogen) protein or portions thereof. Also especially preferred in this regard are conservative substitutions (see below).

Further embodiments of the invention include nucleic acid molecules comprising a polynucleotide having a nucleotide sequence at least 90% identical, and more preferably at least 95%, 96%, 97%, 98% or 99% identical to (a) a nucleotide sequence encoding the delta-plasminogen polypeptide having the complete amino acid sequence in SEQ ID NO: 2; (b) a nucleotide sequence encoding the delta-plasminogen polypeptide having the amino acid sequence in SEQ ID NO:2; and (c) a nucleotide sequence complementary to any of the nucleotide sequences in (a) or (b) above.

By a polynucleotide having a nucleotide sequence at least, for example, 95% "identical" to a reference nucleotide sequence encoding a delta-plasminogen polypeptide is intended that the nucleotide sequence of the polynucleotide be identical to the reference sequence except that the polynucleotide sequence can include up to five point mutations per each 100 nucleotides of the reference nucleotide sequence encoding the delta-plasminogen polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An implementation of this algorithm for nucleic acid and peptide sequences is provided by the Genetics Computer Group (Madison, Wis.) in their BESTFIT utility application. The default parameters for this method are described in the Wisconsin Sequence Analysis Package Program Manual, Version 8 (1995) (available from Genetics Computer Group, Madison, Wis.).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the nucleic acid sequence shown in SEQ ID NO: 1 will encode a delta-plasminogen polypeptide. In fact, because degenerate variants of these nucleotide sequences all encode the same polypeptide, this will be clear to the skilled artisan even without performing any functional assays or measurements described herein It will be further recognized in the art that, for such nucleic acid molecules that are not degenerate variants, a reasonable number will also encode a polypeptide having delta-plasminogen polypeptide activity. This is because the skilled artisan is fully aware of amino acid substitutions that are either less likely or not likely to significantly effect protein function (e.g., replacing one aliphatic amino acid with a second aliphatic amino acid).

Recently, advances in the synthetic production of longer polynucleotide sequences have enabled the synthetic production of nucleic acids encoding significantly longer polypeptides without the use of traditional cloning techniques. Commercial providers of such services include Blue Heron, Inc., Bothell, Wash. Technology utilized by Blue Heron, Inc. is described in U.S. Pat. Nos. 6,664,112; 6,623,928; 6,613,508; 6,444,422; 6,312,893; 4,652,639; U.S. Published Patent Application Nos. 20020119456A1; 20020077471A1; and Published International Patent Applications (Publications Nos) WO03054232A3; WO0194366A1; WO9727331A2; and WO9905322A1, all incorporated herein by reference.

Of course, traditional techniques of molecular biology, microbiology, and recombinant nucleic acid can also be used to produce the polynucleotides of the invention. These techniques are well known and are explained in, for example, Current Protocols in Molecular Biology, F. M. Ausebel, ed., Vols. I, II and III (1997); Sambrook et al., Molecular Cloning: A Laboratory Manual, $2^{nd}$ Edition, Cold Spring Harbor Laboratory Press, Cold Spring Harbor, N.Y. (1989); DNA Cloning: A Practical Approach, D. N. Glover, ed., Vols. I and II (1985); Oligonucleotide Synthesis, M. L. Gait, ed. (1984); Nucleic Acid Hybridization, Hames and Higgins, eds. (1985); Transcription and Translation, Hames and Higgins, eds. (1984); Animal Cell Culture, R. I. Freshney, ed. (1986); Immobilized Cells and Enzymes, IRL Press (1986); Perbal, "A Practical Guide to Molecular Cloning"; the series, Methods in Enzymology, Academic Press, Inc. (1984); Gene Transfer Vectors for Mammalian Cells, J. H. Miller and M. P. Calos, eds., Cold Spring Harbor Laboratory (1987); and Methods in Enzymology, Wu and Grossman and Wu, eds., respectively, Vols. 154 and 155, all incorporated herein by reference.

Vectors and Cultured Host Cells

The present invention also relates to vectors which include the isolated nucleic acid molecules of the present invention, cultured host cells which are genetically engineered with the recombinant vectors, and the production of the delta-plasmin (ogen) polypeptides by recombinant techniques.

Recombinant constructs can be introduced into cultured host cells using well-known techniques such as infection, transduction, transfection, transvection, electroporation and transformation. The vector can be, for example, a phage, plasmid, viral or retroviral vector. Retroviral vectors can be replication competent or replication defective. In the latter case, viral propagation generally will occur only in complementing cultured host cells.

The polynucleotides can be joined to a vector containing a selectable marker for propagation in a cultured host. Generally, a plasmid vector is introduced in a precipitate, such as a calcium phosphate precipitate, or in a complex with a charged lipid. If the vector is a virus, it can be packaged in vitro using an appropriate packaging cell line and then transduced into cultured host cells.

Preferred are vectors comprising cis-acting control regions to the polynucleotide of interest. Appropriate trans-acting factors can be supplied by the cultured host, supplied by a complementing vector or supplied by the vector itself upon introduction into the cultured host.

In certain embodiments in this regard, the vectors provide for specific expression, which can be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

DNA inserts should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate cultured hosts include, but are not limited to, bacterial cells, such as *E. coli*, *Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described cultured host cells are known in the art.

Among vectors preferred for use in bacteria include pQE70, pQE60 and pQE-9, available from Qiagen Inc., Valencia, Calif.; pBS vectors, PHAGESCRIPT vectors, BLUESCRIPT vectors, pNH8A, pNH16a, pNH18A, pNH46A, available from Stratagene, LaJolla, Calif.; and ptrc99a, pKK223-3, pKK233-3, pDR540, pRIT5 available from Pharmacia (now Pfizer, Inc., New York, N.Y.). Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Bacterial promoters suitable for use in the present invention include the *E. coli* lacI and lacZ promoters, the T3 and T7 promoters, the gpt promoter, the lambda PR and PL promoters, and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of a vector construct into the cultured host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology, $2^{nd}$ Edition (1995).

Transcription of the DNA encoding the polypeptides of the present invention by higher eukaryotes can be increased by inserting an enhancer sequence into the vector. Enhancers are cis-acting elements of DNA, usually about from 10 to 300 bp that act to increase transcriptional activity of a promoter in a given cultured host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals can be incorporated into the expressed polypeptide. The signals can be endogenous to the polypeptide or they can be heterologous signals.

The polypeptide can be expressed in a modified form, such as a fusion protein, and can include not only secretion signals, but also additional heterologous functional regions. For instance, a region of additional amino acids, particularly charged amino acids, can be added to the N-terminus of the polypeptide to improve stability and persistence in the cultured host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP 0 464 533 A1 (Canadian counterpart, 2,045,869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties. On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery for example, human proteins have been fused with Fc portions for the purpose of high-throughput screening assays (such as hIL5-receptor, to identify antagonists of hIL-5). See, Bennett, D., et al., *J. Molecular Recognition*, 8:52-58(1995) and Johanson, K. et al., *J. Biol Chem.*, 270(16):9459-9471 (1995).

Delta-plasminogen protein can be recovered and purified from recombinant cell cultures by well-known methods including those specifically described in the examples herein.

Polypeptides of the present invention include naturally purified products, products of chemical synthetic procedures, and products produced by recombinant techniques from a prokaryotic or eukaryotic cultured host, including, for example, bacterial, yeast, higher plant, insect and mammalian cells. In addition, polypeptides of the invention can also include an initial modified methionine residue, in some cases as a result of host-mediated processes.

Polypeptides

The polynucleotides of the invention include those encoding variations and particular examples of the polypeptides of the invention. For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions. Although any number of substitutions within the scope of the invention can be obtained by application of such general principles, for specific guidance regarding substitutions, the references cited herein regarding structure and function of kringle 1 domains can be consulted by one of skill in the art.

It will further be appreciated that, depending on the criteria used, the exact "position" of the kringle 1, activation site, and serine protease domains of the delta-plasminogen polypeptide can differ slightly in particular variations within the scope of the present invention. For example, the exact location of the kringle 1 domain relative to the activation site can vary slightly and/or the sequence N-terminal to the kringle 1 domain can vary in length. Thus, the invention includes such variations of the delta-plasminogen polypeptide which exhibit delta-plasminogen polypeptide activity as disclosed herein. Such variants include deletions, insertions, inversions, repeats, and substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, fragments, derivatives or analogs of the polypeptide of SEQ ID NO: 2 can be (i) ones in which one or more of the amino acid residues (e.g., 3, 5, 8, 10, 15 or 20) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 3, 5, 8, 10, 15 or 20), or (iii) ones in which the mature polypeptide is fused with another compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given delta-plasminogen polypeptide will not be more than 50, 40, 30, 25, 20, 15, 10, 5 or 3.

Amino acids in the delta-plasminogen polypeptide of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity, e.g., as shown in the examples provided herein. Sites that are critical for ligand binding can also be determined by structural analysis such as crystallization, nuclear magnetic resonance or photoaffity labeling (Smith, et al., *J. Mol. Biol.* 224:399-904 (1992) and de Vos, et al. *Science* 255:306-312 (1992)). Even if deletion of one or more amino acids from the N-terminus of a protein results in modification or loss of one or more biological functions of the protein, other biological activities can still be retained.

It is also contemplated that polypeptides useful in production of the "isolated polypeptides" of the invention can produced by solid phase synthetic methods. See Houghten, R. A., *Proc. Natl. Acad. Sci. USA* 82:5131-5135 (1985); and U.S. Pat. No. 4,631,211 to Houghten et al. (1986).

The polypeptides of the present invention can be provided in an isolated form. By "isolated polypeptide" is intended a polypeptide removed from its native environment. Thus, a polypeptide produced and/or contained within a recombinant cultured host cell is considered isolated for purposes of the present invention. Also intended as an "isolated polypeptide" are polypeptides that have been purified, partially or substantially, from a recombinant cultured host.

Polypeptides having an amino acid sequence of an indicated percent identity to a reference amino acid sequence of a delta-plasminogen polypeptide can be determined using the methods, including computer-assisted methods, indicated above regarding polynucleotides. Polypeptide amino acid sequences are examined and compared just as are the nucleotide sequences in the foregoing discussion. One of skill in the art will recognize that such concepts as the molecular endpoints discussed for polynucleotides will have direct analogs when considering the corresponding use of such methods and programs for polypeptide analysis. For example, the manual corrections discussed regarding polynucleotides refer to 5' and 3' endpoints of nucleic acids, but the same discussion will be recognized as applicable to N-termini and C-termini of polypeptides.

The invention encompasses delta-plasminogen polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited, to specific chemical cleavage by cyanogen bromide, trypsin, chymotrypsin, papain, *S. aureus* V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of vectors and constructs adapted for expression of delta-plasminogen polypeptides in prokaryotic cultured host cells. The polypeptides can also be modified with a detectable label, such as an enzymatic, fluorescent, isotopic or affinity label to allow for detection and isolation of the protein.

Pharmaceutical Compositions and Methods of Treatment

Delta-plasmin(ogen) can be formulated for therapeutic use in accordance with the methods and compositions described in US 2003/0012778 A1; and Novokhatny, V., et al., *J. Thromb. Haemost.* 1(5):1034-41 (2003), both incorporated herein by reference. For example, a low-pH (from about 2.5 to about 4), low-buffering capacity buffer can be used for formulation of delta-plasmin. Additionally, other methods and formulations known to those of skill in the art, as practiced with plasmin, mini-plasmin, and/or micro-plasmin, can be used to formulate the delta-plasmin of the invention for therapeutic administration.

The delta-plasmin(ogen) can be used to treat a variety of thrombotic diseases or conditions, for example, according to the methods as described in U.S. Pat. No. 6,355,243; and published U.S. Patent Application Nos. US 2003/0026798 A1; US 2003/0175264 A1, all incorporated herein by reference. Again, as with the possible pharmaceutical formulations applicable to delta-plasmin, delta-plasmin can also be administered therapeutically by methods known in the art, for example, those that may be currently practiced with plasmin, mini-plasmin, and/or micro-plasmin.

Ophthalmic Methods

In addition to general uses associated with plasmin and proteins with plasmin-like enzymatic activity, e.g., thrombolysis, delta-plasmin can be advantageously employed in therapeutic procedures relating to the eye. Such methods include enzymatic vitreolysis and the induction of posterior vitreous detachment. Such methods can be useful in human and animal subjects.

The human eye can be divided into three chambers. The anterior chamber (between the cornea and the iris) and the posterior chamber (between the iris and the crystalline lens) are filled with aqueous humor. In contrast, the vitreous chamber between the crystalline lens and the retina is filled with a more viscous liquid known as the vitreous, the vitreous body, or the vitreous humor. The vitreous humor in a normal eye is a clear gel occupying about 80% of the volume of the eyeball. Light that enters the eye through the cornea, pupil, and lens, is transmitted through the vitreous to the retina.

The vitreous humor of a normal human eye is a gel that is roughly 99% water and 1% macromolecules. These macromolecules include a network of collagen fibrils, hyaluronic acid, soluble glycoproteins, sugars and other low molecular weight metabolites. The posterior portion of the vitreous body, the posterior hyaloid surface (also known as the posterior vitreous cortex), is in direct contact with the inner retinal surface, most prominently at the vitreous base, optic disc, and along the major retinal vessels. Normal adhesion of the vitreous to the retina is mediated by cellular and molecular interactions between the posterior vitreous cortex and the inner limiting membrane (LM) of the retina. The ILM contains collagen types I and IV, glycoproteins such as laminin and fibronectin, and other glycoconjugates. These components are thought to bridge and bind collagen fibers between the vitreous and the ILM.

The process known as "posterior vitreous detachment" (PVD), wherein the vitreous humor changes from gel to liquid, is a normal occurrence after age 40. As the vitreous liquifies, it gradually shrinks and separates from the ILM of the retina. Degenerative changes in the vitreous also may be induced by pathological conditions such as diabetes, Eale's disease, and uveitis. Also, PVD may occur earlier than normal in nearsighted people and in those who have had cataract surgery. Usually, the vitreous makes a clean break from the retina. Occasionally, however, the vitreous adheres tightly to the retina in certain places. These small foci of resisting, abnormally firm attachments of the vitreous can transmit great tractional forces from the vitreous to the retina at the attachment site. These forces can result in horseshoe-shaped tears in the retina. If the retinal tears are not repaired, vitreous fluid can seep through this tear, into or underneath the retina, and cause a retinal detachment—a very serious, sight-threatening condition. In addition, persistent attachment between the vitreous and the ILM can result in bleeding from rupture of blood vessels, which results in the clouding and opacification of the vitreous.

The development of an incomplete PVD has an impact on many vitreoretinal diseases, including vitreomacular traction syndrome, vitreous hemorrhage, macular holes, macular edema, diabetic retinopathy, diabetic maculopathy, and retinal detachment. Thus, an important goal of vitreous surgery is to separate the vitreous from the retina in a manner that prevents vitreous traction.

In order to remove the vitreous from the eye, a microsurgical procedure called vitrectomy is usually performed. In this procedure, the vitreous is removed from the eye with a miniature handheld cutting device while simultaneously replacing the removed vitreous with saline solution to prevent collapse of the eye. Surgical removal of the vitreous using this method is highly skill-dependent, and complete removal of the cortical vitreous remains a difficult task. Furthermore, mechanical vitrectomy carries the risk of complications such as scarring, tearing and other damage to the retina. Such damage is highly undesirable as it can compromise the patient's vision after surgery.

Thus, alternative methods to remove the vitreous from the retina are desirable. Such methods can include the use of enzymes and chemical substances, which can be used to induce/promote liquefaction of the vitreous and/or separation of the vitreoretinal interface (PVD). These approaches may be referred to as "pharmacological" or "enzymatic" vitreolysis or vitrectomy. Delta-plasmin can be used for therapeutic/preventative enzymatic vitrectomy, induction of PVD, or other methods involving partial, complete, or substantially complete vitreolysis.

Delta-plasmin can be used in a methods involving vitreolysis according to procedures and techniques relating to the use of plasmin and plasmin-like molecules. For example, Trese, M., et al. (U.S. Published Patent Application No. 2003/0147877 A1, incorporated herein by reference for its disclosure of techniques and procedures relating to the use of plasmin in vitrectomy) describes general techniques for vitreous liquefaction and vitrectomy using plasmin via injection or sustained release device; and Pakola, S., et al (U.S. Published Patent Application No. 2005/0118158 A1, incorporated herein by reference for its disclosure of techniques and procedures relating to the use of truncated plasmin in vitrectomy) describes techniques of vitreolysis using truncated plasmin-like molecules.

Further guidance regarding use of plasmin or plasmin-like molecules in methods involving vitreolysis can be found in Wang, Z-L, et al., *Retina*, 25:38-43 (2005) (PVD induced by plasmin); Gandorfer, A., et al., *Invest. Ophthalmol. Vis. Sci.*, 45:641-647 (2004) (PVD induced by microplasmin); Wang, F., et al., *Invest. Ophthalmol.*, 45:3286-3290 (2004) (PVD induced by plasmin); Li, X., et al., *Graefe's Arch. Clin. Exp. Opthalmol.*, 240:56-62 (2002) (PVD induced by plasmin); Gandorfer, A., et al., *Br. J. Ophthalmol.*, 55:6-10 (2001) (plasmin assisted vitrectomy); Williams, J. G., et al., *Ophthalmology*, 108:1902-1905 (2001) (PVD induced by autologous plasmin); and Verstraeten, T. C., et al., *Arch. Ophthalmol.*, 111:849-854 (1993) (PVD induced by plasmin), all incorporated herein by reference for their description of techniques of vitreolysis-related procedures using plasmin and plasmin-like enzymes.

Further, the present inventors have found that delta-plasmin is well-suited for ophthalnic methods relating to vitreolysis. For example, experiments have shown that when plasmin and delta-plasmin are incubated with bovine vitreous humor, delta-plasmin produces a solution of greater clarity (less precipitation) than plasmin. Also, incubation of porcine vitreous humor with delta-plasmin results in a greater reduction of high molecular weight proteinaceous species relative to plasmin, as shown by reducing and non-reducing gel electrophoresis. See the Examples below for additional details.

It will be clear that the invention may be practiced otherwise than as particularly described in the foregoing description and the following examples. Numerous modifications and variations of the present invention are possible in light of the teachings herein and, therefore, are within the scope of the invention.

EXAMPLES

Expression Vector Design

The amino acid sequence for delta-plasminogen is shown in SEQ ID NO:2. A putative sequence encoding delta-plasminogen was codon-optimized for *E. coli* expression and mRNA stability to produce the DNA sequence as shown in SEQ ID NO:1.

This DNA was chemically synthesized (Blue Heron, Inc,) and inserted into the NdeI and BamH1 sites of *E. coli* expression vector pET22b(+) (Novagen; Madison, Wis.) in order to produce cytosolic protein. This construct produces delta-plasminogen with an additional, non-native N-terminal methionine. (pET-22b(+)=pET Expression System 22b (Cat. No. 70765), EMD Biosciences, Inc., Novagen Brand, Madison, Wis.; see http://www.emdbiosciences.com product information section regarding pET-22b for details regarding vector).

Delta-Plasminogen Expression and Purification

The DNA encoding delta-plasminogen sequence was transformed into a variety of cells, and protein over-expression following induction by 1 mM IPTG (isopropyl-beta-D-thiogalactopyranoside) was analyzed by SDS-PAGE. Cell type BL21(DE3) RIL (Stratagene, La Jolla, Calif.) cells, engineered to express rare *E. coli* tRNAs coding for Arg, Ile, and Leu, were used for production of delta-plasminogen.

Production of delta-plasminogen was confirmed in larger scale expression in which cells were lysed and both soluble protein and purified inclusion bodies were examined by SDS-PAGE. BL21(DE3) RIL cells produced significant delta-plasminogen protein in the form of inclusion bodies. Expression estimates were 50-80 mg/L cell culture.

The following typical protocol has been used for expression of delta-plasminogen:

A single colony of BL21 (DE3) RIL cells containing the delta-plasminogen vector was used to inoculate 5 ml of LB/ampicillin (100 μg/ml)/chloramphenicol (50 μg/ml) and was incubated for 8 hours at 37° C. on a shaker. After that, a 50 μl-aliquot was taken form the cultured bacterial suspension for further growth in fresh media. The procedure was repeated after 16 hours with 6 ml of bacterial culture and 250 ml of the media. Cultures were grown at 37° C. with shaking to an OD600 nm of ~1.0, and IPTG was added to 1 mM final concentration. Cultures were grown for an additional 5 hours. Cells were harvested by centrifugation at 5,000×g and cell pellets were dissolved in 20 mM Tris pH 8.0 containing 20 mM EDTA and frozen at −80° C.

To purify delta-plasminogen, cell pellets were thawed and buffer added until the solution volume was approximately 1/20th that of the original cell culture volume. After that, lysozyme was added to a final concentration of 0.5 mg/ml and the cells were stirred rapidly at 4° C. for 10-15 minute. Then, Triton X-100 was added to 1% final concentration and stirring continued for another 10 min. DNAse I (0.05 mg/ml) and MgCl$_2$ (2.5 mM) were added and stirring was continued at 4° C. for 30 minutes or until the solution was no longer viscous. The final solution was centrifuged at 4° C. for 30 min at 15,000×g and the supernatant was discarded.

The cell pellet was washed three times with wash solution (50 mM Tris-HCl, pH 7.4 containing 10 mM EDTA, 1% Triton-X-100, and 0.5 M urea), and the final pellet was dissolved in 40 ml of extraction buffer (PBS, pH 7.4 containing 10 mM EDTA, 20 mM DTT, and 6 M guanidine-HCl) and stored at 4° C. overnight. After 16 hours, the solution was centrifuged for 30 minutes at 15,000×g to remove solids and the supernatant was slowly added to the refolding solution (50 mM Tris-HCl, pH 8.3, 3.5 M guanidine HCl, 0.5 M arginine HCl, 10 mM EDTA, 3 mM GSH, 0.3 mM GSSG) while stirring at 4° C. The refolding procedure was carried out at protein concentration of 0.03 mg/ml or less.

The refolding solution was kept for 2 days at 4° C. undisturbed and then dialyzed against an 8-fold volume of 0.1 M Tris-HCl pH 8.0 containing 10 mM EDTA, 0.15 M NaCl, 0.15 M arginine-HCl, over a period of 8-10 hours with frequent changes of the buffer solution.

The protein solution was then removed from dialysis and concentrated using AMICON filters with the membrane cut-off of 10 kDa to approximately 10-20 ml and dialyzed overnight versus a 100-fold volume of 0.1 M Tris pH 8.0 containing 10 mM EDTA, 0.15 M NaCl. This material was centrifuged to remove particulates, then passed over lysine affinity resin (Lysine-SEPHAROSE 4B; Amersham Biosciences, Piscataway, N.J.). Delta-plasminogen was eluted from the resin using Tris-buffered saline, pH 8.0 containing 0.2 M epsilon aminocaproic acid (εACA).

Typically, 80 mg of inclusion bodies could be isolated from 1 liter of cell culture and 40 mg could be eluted in the lysine-SEPHAROSE chromatography step.

Properties of Delta-Plasminogen

Purified delta-plasminogen appeared as a single band in the 35-40 kDa region by SDS-PAGE analysis of reduced (dithiothreitol-treated) and non-reduced protein (See FIG. 5). Its exact molecular mass, determined by MALDI mass-spectrometry, was 37,089 Da, very close to the expected value of 37,198 Da.

Figure 6:
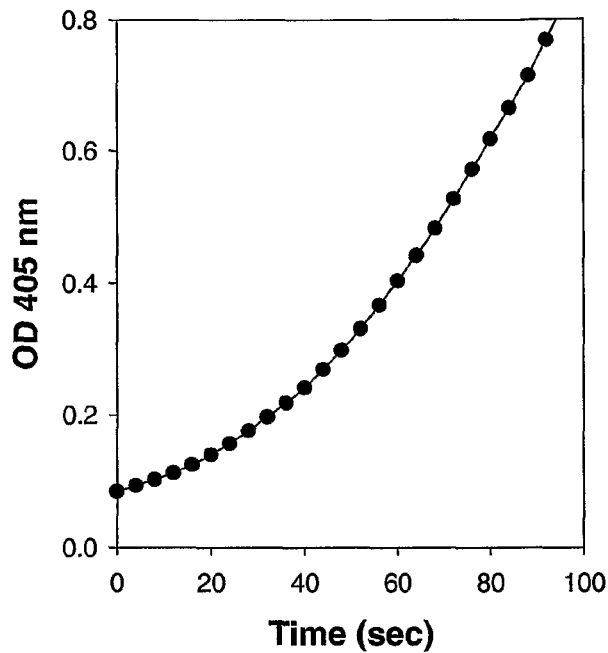
FIG. 6 is a graphic representation of activation of delta-plasminogen by urokinase. Urokinase (5.8 nM) was added to a solution of 5 µM delta-plasminogen in PBS containing 1.0 mM S-2251 at 37° C. Increases in absorbance were monitored at 405 nm.

To test whether delta-plasminogen (ΔPg) could be activated into delta-plasmin, delta-plasminogen was incubated with urokinase (1:1000 molar ratio), and the increase in serine protease activity was monitored by measuring the increase in the rate of S-2251 hydrolysis (S-2251=D-Val-Leu-Lys-p-nitroanilide, DiaPharma Group, Inc., West Chester, Ohio). As seen in FIG. 6, a parabolic increase in activity typical for the coupled reaction of activation (zymogen is converted into active enzyme (1); and enzyme cleaves the chromogenic substrate (2)) is observed. Activation of delta-plasminogen to delta-plasmin was complete within 3 minutes under these conditions. Very similar results were obtained with tPA and streptokinase.

The kinetics for the urokinase activation of delta-plasminogen were compared to those for full-length plasminogen using the method of Wohl et al. (Wohl, R. C., Summaria, L., Arzadon, L., and Robbins, K. C.; *J. Biol. Chem.* 253: 1402-1407 (1978), fully incorporated by reference). For this purpose, 5.8 nM urokinase was added to solutions containing various concentrations of plasmin species in the presence of 1 mM S-2251 substrate at 37° C., pH 7.5. The increase in absorbance at 405 nm was monitored and the accelerating rate of S-2251 product formation was calculated using a parabolic equation where rate=k·t$^2$. Data were fit to a Michaelis-Menten kinetic model using Lineweaver-Burk analysis, resulting in the values below:

TABLE 1

Kinetics for the urokinase activation of delta-plasminogen.

| Species: | $K_m$ (μM) | $k_{cat}$ (min$^{-1}$) | $k_{cat}/K_m$ (μM$^{-1}$min$^{-1}$) |
|---|---|---|---|
| Delta-plasminogen | 30 +/− 5 | 80 +/− 10 | 2.67 |
| Plasminogen | 1.2 +/− 0.1 | 2.3 +/− 0.3 | 1.92 |

Full-length plasminogen was activated well by urokinase, with Km values similar to those found in the literature (1.7 μM; Wohl, R. C., Summaria, L., and Robbins, K. C.; *J. Biol. Chem* 255(5): 2005-2013 (1980)) and equivalent kcat values.

Km values for urokinase activation of delta-plasminogen were approximately 30-fold higher than for plasminogen, possibly indicating a lower affinity of urokinase for this mutant of plasminogen. At the same time, the $k_{cat}$ value for activation of delta-plasminogen was much higher than for plasminogen. In spite of the above-mentioned differences in the $k_{cat}$ and $K_m$, their ratio, or catalytic efficiency, is approximately the same for activation of the natural and recombinantly-modified plasminogen species by urokinase. Thus, these data indicate that the presence of a "foreign" kringle 1 does not considerably affect the activation properties of the serine protease domain in delta-plasminogen.

In yet another activation experiment, delta-plasminogen was incubated with streptokinase, tPA, and urokinase and analyzed on reduced SDS-PAGE to observe the conversion of the one-chain delta-plasminogen molecule in two-chain delta-plasmin (See FIG. 5, Lanes 3-5). In all three cases, two chains (~12 kDa kringle 1 and the ~25 kDa serine protease chain) of delta-plasmin could be seen, suggesting that delta-plasminogen indeed can be activated by all three plasminogen activators.

Figure 7:
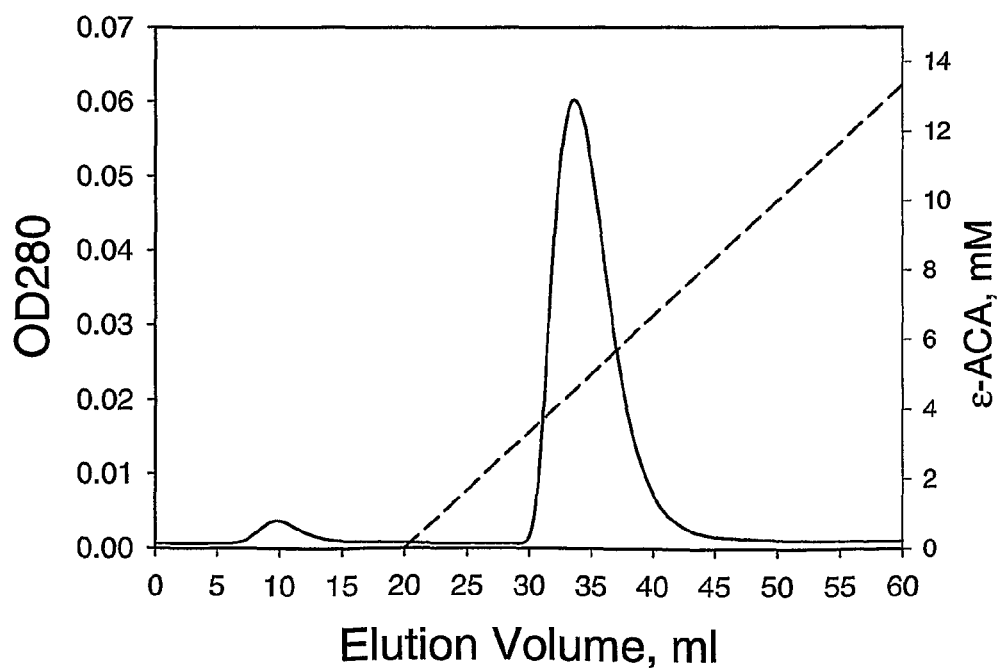
FIG. 7 is a chromatogram showing binding of delta-plasminogen to lysine-SEPHAROSE 4B: 0.5 mg of purified delta-plasminogen was applied on the lysine-SEPHAROSE 4B column (1×3 cm) equilibrated with Tris-buffered saline, pH 7.4. Bound protein was eluted from the column by a 0-20 mM gradient of ϵ-aminocaproic acid (ϵ-ACA) as a single peak. The absorbance at 280 nm and the concentration of ϵ-ACA, as a function of the effluent volume are presented on the graph.

As expected, delta-plasminogen bound to lysine-SEPHAROSE via kringle 1 and could be eluted from the column by the gradient of εACA as a single peak (See FIG. 7). The ability of refolded delta-plasminogen to bind lysine-SEPHAROSE indicates that the kringle domain of the molecule is properly folded and the lysine-binding site is fully active.

To further confirm the functionality of kringle 1, the binding of εACA to delta-plasminogen was measured by monitoring the associated changes in protein fluorescence as described by Matsuka et al. (Matsuka, Y. V., Novokhatny, V. V., and Kudinov, S. A., *Eur. J. Biochem.* 190:93-97 (1990)) and Douglas et al. (Douglas, J. T., von Haller, P. D., Gehrmann, M., Llinas, M., and Schaller. J., *Biochemistry* 41:3302-3310(2002), all incorporated herein by reference). Binding of εACA to kringle 1 of delta-plasminogen results in a decrease in fluorescence, likely due to quenching of the tryptophan residues which are part of the lysine-binding site.

To monitor this process, 4 μl to 16 μl aliquots of a concentrated solution of εACA were added to 2 ml of 5 μM delta-plasminogen in 50 mM Tris buffer containing 20 mM NaCl, pH 8.0, 25° C. The fluorescence was monitored at an excitation wavelength of 298 nm and an emission wavelength of 340 nm in a FLUOROMAX fluorescence spectrophotometer (Jobin Yvon, Inc., Edison, N.J.); after each addition of εACA, the solution was allowed to equilibrate until no further changes in fluorescence were observed.

The resulting fluorescence values were corrected for dilution and plotted versus the concentration of εACA over a range of 0-50 µM εACA. Data were fitted by non-linear regression to obtain a $K_d$ of 11.1±2.3 µM, in good agreement with literature values for kringle 1 affinity for εACA of 3.2 µM (Matsuka, et al.) and 13 µM (Douglas, et al.).

One property of plasmin is its ability to bind fibrin. In order to determine whether delta-plasminogen retains the ability to interact with fibrin, its fibrin-binding properties were tested in a microtiter plate assay in which binding of delta-plasminogen to fibrin was assessed by its subsequent activation by tPA and resulting clot lysis. For this purpose, 100 µl of 5 mg/ml fibrinogen was polymerized with thrombin in each well of a microtiter plate. Various concentrations of delta-plasminogen were added on top of the fibrin clots and incubated for 1 hour at 37° C. The plate was washed extensively with PBS while the fibrin clots were still intact and attached to the wells. After washing, a 0.1-mg/ml solution of tPA was added to each well and the plate was incubated 2 hours at 37° C. As a result, some of the clots were completely dissolved and some were partially dissolved, while wells with very low amounts of delta-plasminogen and control wells remained practically intact. The degree of fibrinolysis was monitored by measuring the 280 nm absorbance of remainders of the initial clots reconstituted in 1M NaOH. The absorbance values were plotted as a function of delta-plasminogen concentration.

Figure 8:
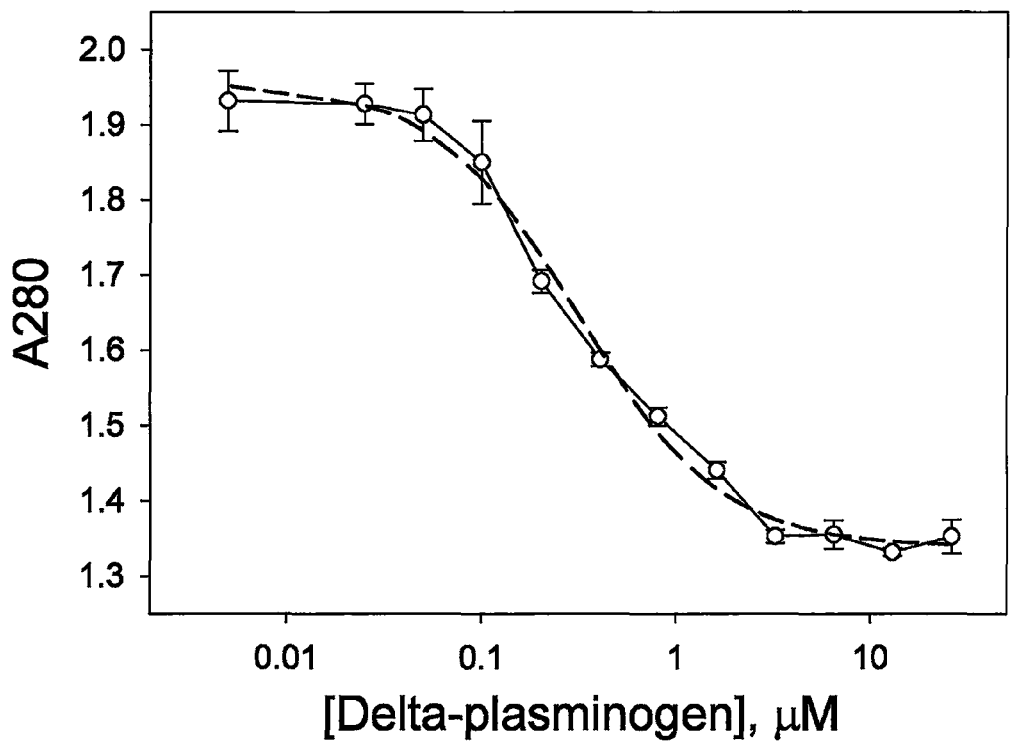
FIG. 8 shows binding of delta-plasminogen to fibrin. Varying concentrations of delta-plasminogen were incubated with fibrin clots in a microtiter plate for 1 hour at 37° C. After incubation the clots were washed extensively with PBS and a 0.1 mg/ml solution of tPA was added to each well. After a 2-hour incubation at 37° C. the liquid was removed and remaining solid clots were reconstituted with 100 µl of 1M NaOH. The amount of remaining fibrin was quantified by measuring the 280 nm absorbance of these reconstituted clots. The degree of fibrinolysis, which is a result of delta-plasminogen binding to fibrin, was plotted on the graph as a function of delta-plasminogen concentration (solid line). The dash line represents the best fit of experimental data to a binding equation.

As seen in FIG. 8, the binding of delta-plasminogen to fibrin follows a classic, sigmoidal binding curve. Using this assay, it was found that delta-plasminogen binds fibrin with affinity comparable to that of full-length plasminogen and the $C_{50}$ of this interaction (~0.2 µM) is comparable to the $K_d$ of fibrin-binding of full-length plasminogen (Lucas, M. A., Fretto, L. J., and McKee, P. A.; *J. Biol. Chem.* 258(7): 4249-4256 (1983)). These experiments indicate that delta-plasminogen can bind fibrin.

Thus, the interaction of delta-plasminogen with lysine-SEPHAROSE, its ability to bind εACA with the expected $K_d$, its ability to bind fibrin, its ability to be activated by all major plasminogen activators, and the potency of delta-plasmin toward the chromogenic plasmin substrate S-2251 all indicated that this molecule was produced in the *E. coli* system in a fully functional form.

Delta-Plasmin Purification and Formulation

Delta-plasminogen, dialyzed against 0.1M Tris buffer, pH 8.0 containing 10 mM EDTA and 0.15 M NaCl, was activated to delta-plasmin using urokinase immobilized on SEPHAROSE 4B essentially as described previously for plasmin (Marder, V. J., et al., *Thromb Haemost.*, 86(3):739-45 (2001), incorporated by reference). Activation occurred at room temperature and was monitored in real time by the increase in S-2251 activity. Depending on the amount of delta-plasminogen, which varied from batch to batch (typically 1-2 mg/ml), incubation time was 30-60 min. Upon completion of activation, when the S-2251 activity reached a plateau, urokinase-SEPHAROSE was filtered out and active delta-plasmin was captured on benzamidine-SEPHAROSE (Pharmacia). Delta-plasmin was eluted from the resin using low-pH buffer (0.2 M glycine, pH 3.0, 0.3 M NaCl, 0.2M εACA).

Figure 9:
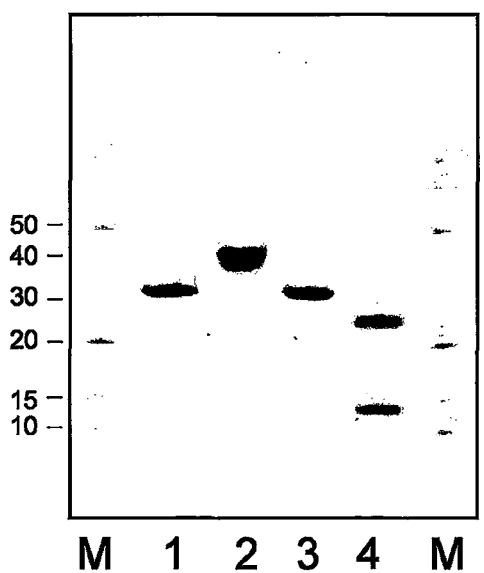
FIG. 9 shows a 8-25% gradient SDS-PAGE of starting delta-plasminogen under non-reduced (Lane 1) and reduced conditions (Lane 2) and final delta-plasmin preparation, also under non-reduced (Lane 3) and reduced (Lane 4) conditions.
Figure 10:
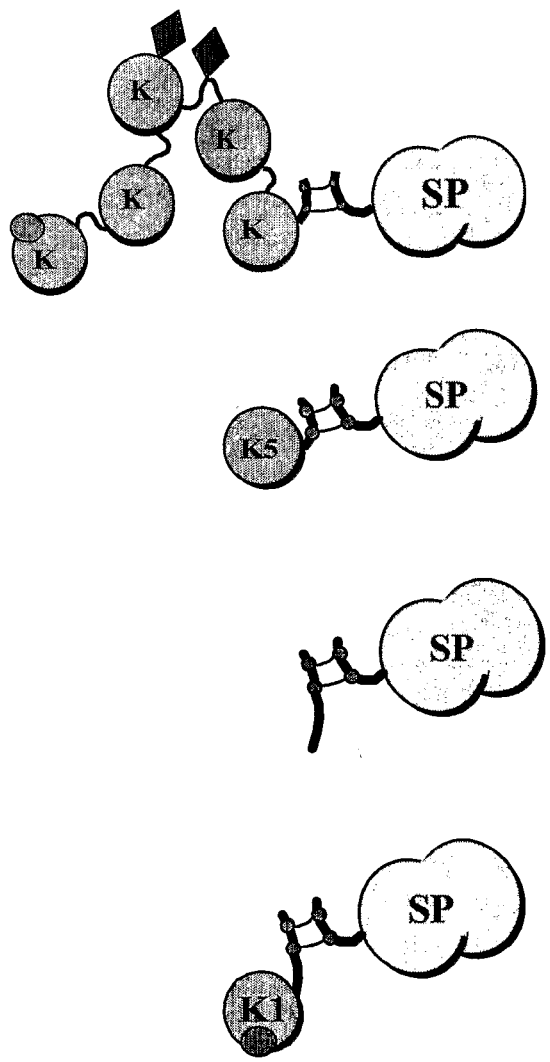
FIG. 10 shows schematic diagrams of plasmin, mini-plasmin, micro-plasmin, and delta-plasmin, along with a corresponding characterization of enzymatic activity ($k_{cat}$ and $K_M$ with respect to substrate S-2251 (D-Val-Leu-Lys-p-nitroanilide, DiaPharma Group, Inc., West Chester, Ohio)).

The protein concentrations and S-2251 activity in elution fractions were measured. High specific activity fractions were pooled and dialyzed against multiple changes of 0.15 M NaCl, pH 3.6 at 4° C. SDS-PAGE analysis of non-reduced delta-plasmin samples (see FIG. 9, Lane 3) shows that the purity of this material is usually more than 95%. Under reduced conditions (FIG. 9, Lane 4), besides the serine protease and the kringle chains, there are two faint bands above and below the kringle band. These bands represent auto-degradation products of the serine protease domain which result from internal cleavages of its polypeptide chain; they are normally held together by disulfide bonds but become visible with PAGE under reducing conditions. The amount of auto-degradation products, which typically did not exceed 10%, was greatly reduced by conducting the benzamidine-SEPHAROSE purification step in batch mode instead of the column format.

Because delta-plasmin, similar to full-length plasmin, is prone to auto-degradation at physiological pH, pH 3.6 was chosen for the final formulation (acidified with acetic acid-saline). As shown previously for plasmin (Novokhatny, V. et al., *J. Thromb Haemost.*, 1(5):1034-41 (2003), incorporated by reference) and confirmed in experiments with delta-plasmin, this low buffering-capacity, low pH formulation not only allows safe storage of active plasmins for prolonged periods of time, but is also compatible with parenteral administration of these direct thrombolytics. When mixed with plasma or neutral pH buffers, delta-plasmin is quickly re-activated.

Enzymatic Properties of Delta-Plasmin

The amidolytic activity of delta-plasmin was examined using the plasmin substrate D-Val-Leu-Lys-p-nitroanilide (S-2251) (DiaPharma, West Chester, Ohio). At pH 7.4, 25° C. in PBS buffer, the Michaelis-Menten constant (Km) for S-2251 was found to be 138 µM (Table 2). The kcat for the preparation was found to be 510 min$^{-1}$. Using 4-nitrophenyl 4-guanidinobenzoate hydrochloride (PNPGB) titration (Chase, T. and E. Shaw, *Methods Enzymol.* 197:20-27 (1970)), the percent of functional active sites was found to be 67%. Correcting kcat for percent active sites, a kcat of 755±45 min$^{-1}$ was determined. This value was very close to the value determined in the same assay for full-length plasmin, 760±23 min$^{-1}$ and for micro-plasmin (lacking all five kringles), 795±24 min$^{-1}$ (See FIG. 9). These data indicate that presence or absence of kringles does not affect the catalytic activity of the serine protease domain.

The rate of inhibition of delta-plasmin by $\alpha_2$-macroglobulin was measured using the method of Anonick et al. (Anonick, P., et al., *Thrombosis Res.* 59:449-462 (1990)). The inhibition rate was found to be 7.6±0.6×10$^5$ M$^{-1}$s$^{-1}$ at 22° C. in PBS buffer.

The rate of inhibition of delta-plasmin by $\alpha_2$-antiplasmin was determined to be 1.1×10$^7$ M$^{-1}$s$^{-1}$ using the method of Wiman and Collen (Wiman, B. and D. Collen, *Eur. J. Biochem.* 84:573-578 (1978)) in which plasmin and $\alpha_2$-antiplasmin are mixed then assayed for S-2251 activity at specific time points (Table 3). This value is comparable to reported values for plasmin of 2.5×10$^7$ M$^{-1}$s$^{-1}$ (from Anonick, et al., *Thrombosis Res.* 59:449 (1990)).

The same experiments conducted with micro-plasmin revealed $\alpha_2$-antiplasmin inhibition rates of 1.8×10$^5$ M$^{-1}$s$^{-1}$ and 3.1×10$^5$ M$^{-1}$s$^{-1}$ in two separate experiments. The rate of $\alpha_2$-antiplasmin inhibition of mini-plasmin (mini-plasmin domain composition, K5-SP) was determined to be 2.4×10$^5$ M$^{-1}$s$^{-1}$. These data are in reasonable agreement with literature values for micro- and mini-plasmin and show that inhibition of delta-plasmin by $\alpha_2$-antiplasmin is 40-fold faster than the inhibition of either micro-plasmin or mini-plasmin. Thus, these results indicate that delta-plasmin should be rapidly inhibited by $\alpha_2$-antiplasmin due t6 the presence of kringle 1 in its structure.

Overall, the data presented in this section show that the enzymatic and inhibitory properties of delta-plasmin are similar to full-length plasmin.

TABLE 2

Steady-state kinetic parameters for various plasmin species with substrate S-2251, in PBS buffer, pH 7.4, 25° C.

|  | $K_m$ | $k_{cat}$ |
|---|---|---|
| plasmin | 193 +/− 7 µM | 760 +/− 23 min$^{-1}$ |
| mini-plasmin | 160 +/− 30 µM | 770 +/− 70 min$^{-1}$ |
| micro-plasmin | 145 +/− 13 µM | 795 +/− 24 min$^{-1}$ |
| delta-plasmin | 138 +/− 5 µM | 755 +/− 45 min$^{-1}$ |

TABLE 3

Inhibition rates for various plasmin species and inhibitors were determined at 22° C. in PBS buffer, pH 7.4.

|  | $\alpha_2$-macroglobulin | $\alpha_2$-antiplasmin |
|---|---|---|
| plasmin | 6.5 +/− 0.5 × 10$^5$ M$^{-1}$s$^{-1}$ | 2.5 +/− 0.5 × 10$^7$ M$^{-1}$s$^{-1}$ (lit.) |
| mini-plasmin | 7.5 +/− 0.3 × 10$^5$ M$^{-1}$s$^{-1}$ | 2.4 +/− 0.5 × 10$^5$ M$^{-1}$s$^{-1}$ |
| micro-plasmin | 7.8 +/− 0.6 × 10$^5$ M$^{-1}$s$^{-1}$ | 1.8 +/− 0.2 × 10$^5$ M$^{-1}$s$^{-1}$ |
| delta-plasmin | 7.6 +/− 0.6 × 10$^5$ M$^{-1}$s$^{-1}$ | 1.0 +/− 0.1 × 10$^7$ M$^{-1}$s$^{-1}$ |

Literature values are taken from Anonick, et al., *Thrombosis Res.* 59:449(1990). All rates were measured according to the methods published in Anonick, et al.

In Vitro Thrombolytic Efficiency

The thrombolytic efficacy of delta-plasmin was tested in an in vitro model of catheter-assisted thrombolysis (Novokhatny, V. et al., *J Thromb Haemost.*, 1(5):1034-41 (2003), incorporated by reference) using the following experimental protocol.

Fresh whole human blood was collected into 20×0.95 cm glass tubes and allowed to clot spontaneously without additives. Tubes were incubated for 20 hr at 37° C. to allow full retraction. Retracted clots were separated from serum using USA Standard testing sieves D16 with 14 mesh, and their weights were determined. Blood clots were transferred into smaller diameter glass tubes in which the retracted clots fit tightly (0.8×7 cm). The averaged weight of the clots was ~3.6 g.

Single 1-ml doses of acidified saline, plasmin, or delta-plasmin were injected into the clot using a syringe. The clots were incubated for 1 hour at 37° C. in a THELCO laboratory oven (Jouan, Inc., Winchester, Va.). After the incubation, the clots were placed again on the sieve to remove the liquefied material and the weight of the digested clots was measured. The extent of clot lysis was determined from the difference between the initial clot weight and the weight of residual clot and was expressed as a percent of clot weight reduction.

Figure 11:
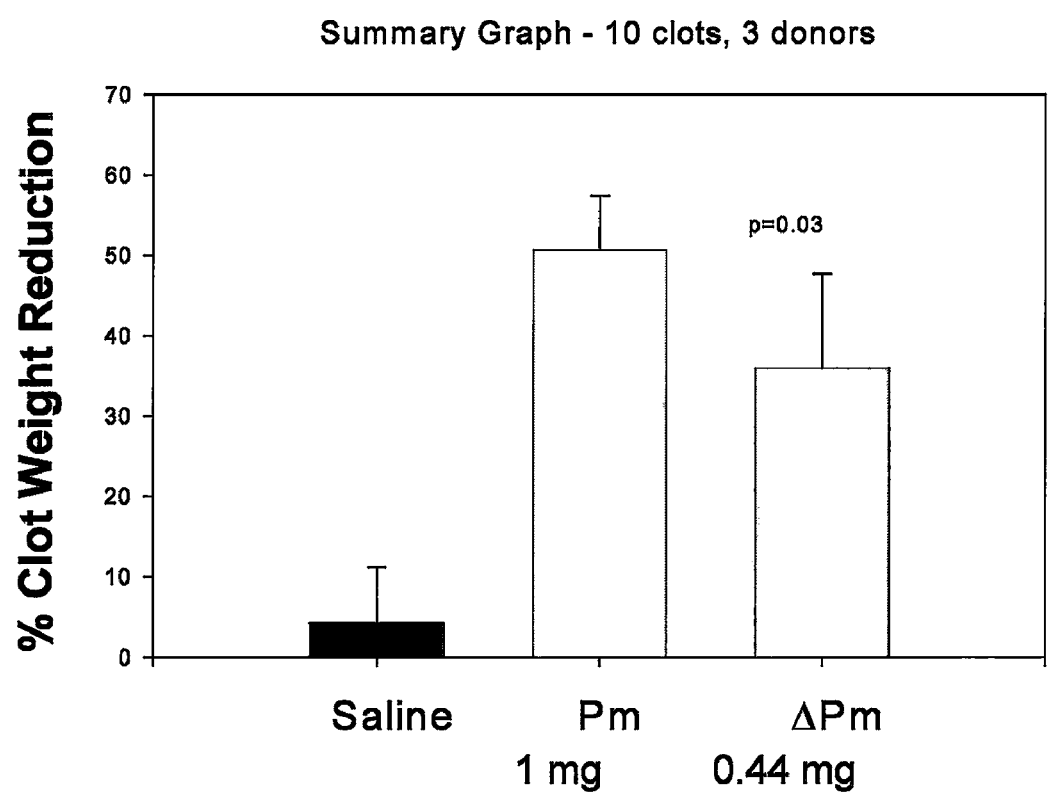
FIG. 11 is a graphic representation of delta-plasmin-induced lysis of retracted whole-blood clots. Each clot (0.8×7 cm) was injected with a 1 ml volume of vehicle (acidified saline, pH 3.6), plasmin (1.0 mg/ml), or delta-plasmin (0.44 mg/ml), and clot dissolution was allowed to proceed at 37° C. for 1 hour.

FIG. 11 shows the results of the lysis experiments with delta-plasmin in this model. The infusion of single 0.44 mg (equivalent to 1 mg/ml of plasmin on a molar basis) dose of delta-plasmin resulted in 36% clot weight reduction within 60 min. At the same time, the weight of the clots infused with saline decreased only by 4%. Plasmin (1.0 mg) resulted in 50% clot weight reduction in the same period. Thus, these data show that delta-plasmin exhibits thrombolytic potency and can be used as a direct thrombolytic agent.

In Vitro Analysis of Delta-Plasmin Activity Related to Ophthalmic Use

Precipitation of plasmin and delta-plasmin by hyaluronic acid, one of the main components of the vitreous humor, was examined. Also, vitreolytic effects of plasmin and delta-plasmin were shown and compared via electrophorectic analyses of the results of incubation of those enzymes with porcine vitreous humor.

Figure 12:
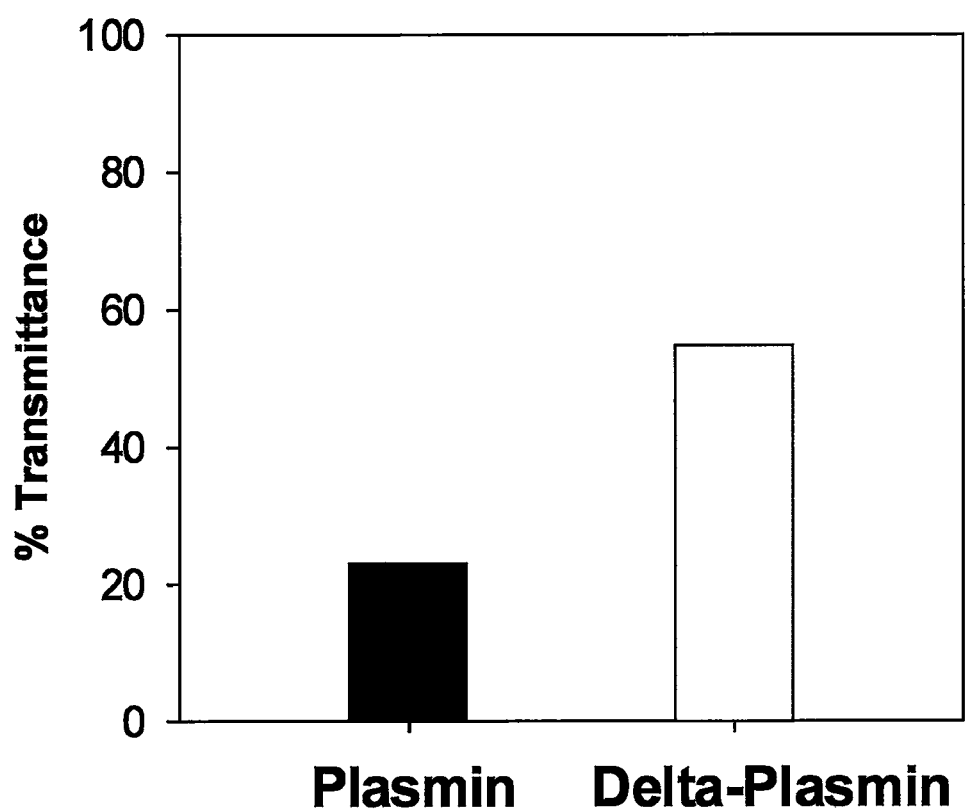
FIG. 12 is a graph comparing precipitation of plasmin and delta-plasmin by hyaluronic acid, one of the main components of the vitreous humor. Equimolar amounts of plasmin (1 mg/ml) and delta-plasmin (0.44 mg/ml) formulated at low-buffering capacity, low pH buffer were incubated with 0.2% Hyaluronic acid (HA), pH 6.5 from bovine vitreous humor for 1 hour at room temperature and % transmittance at 580 nm was measured. The diluent was saline.

Equimolar amounts of plasmin (1 mg/ml) and delta-plasmin (0.44 mg/ml) formulated at low-buffering capacity, low pH buffer were incubated with 0.2% Hyaluronic acid (HA), pH 6.5 from bovine vitreous humor for 1 hour at room temperature and % transmittance at 580 nm was measured. The diluent was saline. As indicated in FIG. 12, the solution incubated with delta-plasmin was significantly clearer.

Figure 13:
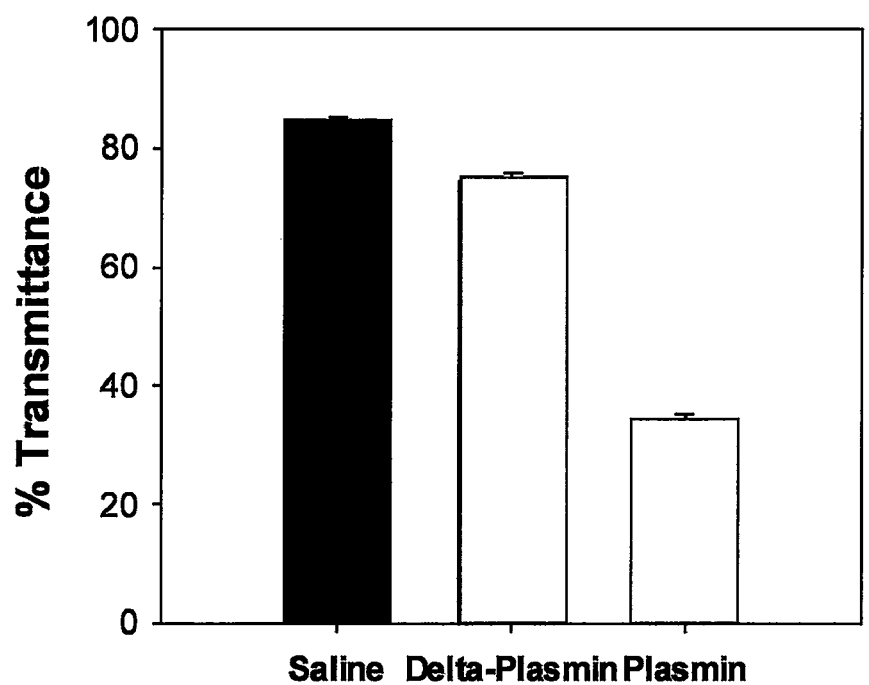
FIG. 13 is a graph comparing turbity of equimolar amounts of plasmin (1 mg/ml) and delta-plasmin (0.44 mg/ml) formulated at low-buffering capacity, low pH buffer and saline (control), mixed with porcine vitreous humor at 1:1 volume ratio.

In another experiment, equimolar amounts of plasmin (1 mg/ml) and delta-plasmin (0.44 mg/ml) formulated at low-buffering capacity, low pH buffer and saline (control), were mixed with porcine vitreous humor at 1:1 volume ratio and the turbidity of the resulting mixture was measured in a microtiter plate reader after 6 min incubation at 37° C. While the clarity of the vitreous mixed with saline or delta-plasmin remained unchanged, the mixture of plasmin with the vitreous was visually cloudy. The results of this experiment are shown in FIG. 13.

Further, equimolar amounts of plasmin (1 mg/ml) and delta-plasmin (0.44 mg/ml) formulated at low-buffering capacity, low pH buffer were mixed with porcine vitreous humor (2 parts of vitreous humor+1 part of enzyme solution) and incubated for 2 hours at 37° C. Samples were taken at indicated times points.

Figure 14:
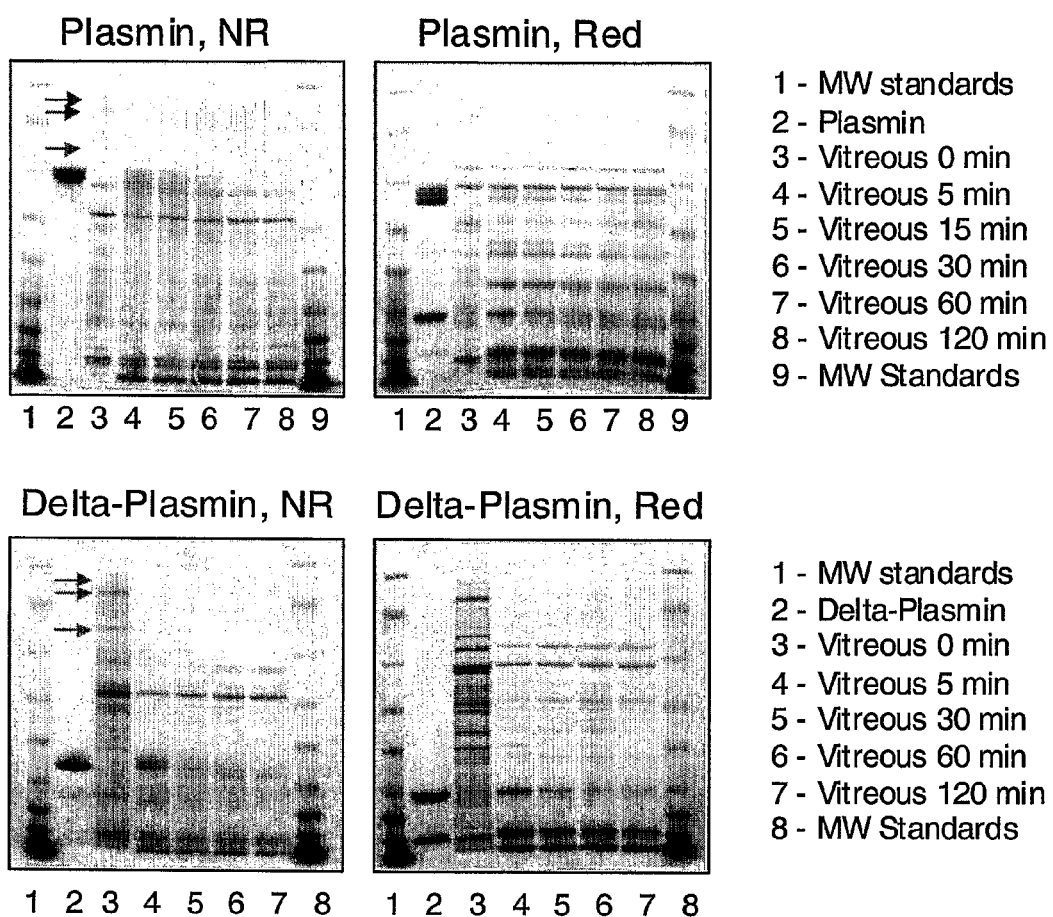
FIG. 14 shows electrophoretic analyses of vitreolysis by plasmin and delta-plasmin. Equimolar amounts of plasmin (1 mg/ml) and delta-plasmin (0.44 mg/ml) formulated at low-buffering capacity, low pH buffer were mixed with porcine vitreous humor (2 parts of vitreous humor +1 part of enzyme solution) and incubated for 2 hours at 37° C. Samples were taken at indicated times points. Vitreolysis is indicated by the progressive disappearance of the high-molecular weight bands (arrows) seen both on the non-reduced (NR) and reduced (Red.) gels.

FIG. 14 shows electrophoretic analyses of vitreolysis by plasmin and delta-plasmin. Vitreolysis was indicated by the progressive disappearance of the high-molecular weight bands (arrows), as can be seen on the non-reduced (NR) and reduced (Red.) gels.

Delta-Plasmin as an Adjunct to Surgical Vitrectomy

A patient presenting vitreoretinal disease in which surgical vitrectomy is indicated is treated with an injection of delta-plasmin prior to the surgical vitrectomy procedure. The patient is to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements.

Either up to 30 minutes or up to 1 day prior to the start of vitrectomy, the eye to be treated is injected with 0.025 to 0.125 mg of delta-plasmin in 0.2 ml of the intraocular irrigating solution, balance salt solution (BSS PLUS® Intraocular Irrigating Solution, Alcon Laboratories, Inc., Fort Worth, Tex.), or other irrigating solution to promote the liquefaction of the vitreous and/or induce posterior vitreous detachment.

By promoting liquefaction of the vitreous and/or posterior vitreous detachment, the surgical vitrectomy can be made quicker and easier with less iatrogenic retinal trauma and risk of surgical complications. Allowing for more complete removal of vitreous may also lessen the risk of post-operative complications such as proliferative vitreoretinopathy.

Treatment of Diabetic Retinopathy with Delta-Plasmin Without Vitrectomy

In this Example, a diabetic patient manifesting diabetic retinopathy is treated by the intravitreal injection of delta-plasmin.

The diabetic patient is to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements.

Following the preliminary examination, an intravitreal injection of delta-plasmin is given to the patient's affected eye. If both eyes are affected, they may be treated separately.

The eye to be treated is injected with a dose ranging from 0.005 mg to 0.125 mg of delta-plasmin in 0.05 to 0.2 ml of BSS PLUS®, or other irrigating solution intravitreally to promote the liquefaction of the vitreous.

After treatment, the patients' eyes are to be examined periodically. The extent of diabetic retinopathy presented by the patient is continuously monitored through periodic retinal examinations and fluorescein angiograms to monitor the extent of venous beading, IRMA, retinal ischemia, traction retinal detachment, vitreous hemorrhage, need for vitrectomy, or other complications of diabetic retinopathy.

Vitreolysis in Porcine Cadaver Eyes

A pilot study determined that an intravitreal injection of plasma-derived human plasmin (h-plasmin) resulted in vitreolysis on fresh porcine cadaver eyes as determined by high-frequency ultrasound. These experiments compare vitreolysis induced by intravitreal injections of h-plasmin to recombinant plasmin (r-plasmin: r-plasmin is delta-plasmin).

Fresh porcine cadaver eyes, obtained within 24 hours of death, were used. Intravitreal injections were made using a 27 G needle. The injections were made in the posterior vitreous adjacent to the retina. The posterior vitreous and the vitreoretinal junction were imaged using high-frequency 35 MHz ultrasound (E Technologies, Optikon 2000, Iowa). Images were recorded from the superior retina, adjacent to the optic nerve head.

For the dose response study, 3 doses of h-plasmin and 3 of r-plasmin were evaluated. The doses and volumes included 50, 100, and 200 µl of sample. Five eyes for each dose were injected and ultrasound images were collected immediately prior to the vitreal injection, and at times 1, 3, 5, 10, 15, and 30 minutes after injection. Intravitreal injections of saline (pH 3.6) at equal volume were used as controls (n=5). Statistical comparisons were made between the groups in percent of posterior vitreal detachment (PVD), time to PVD, and time to total vitreal dissolution. A total of 35 eyes were used for this study. Statistical analysis was performed using the JMP computerized statistical program (SAS, Inc. Cary, N.C.). ANOVA and Tukey's HSD test were used. Significant differences were noted with a $P<0.05$.

Figure 15:
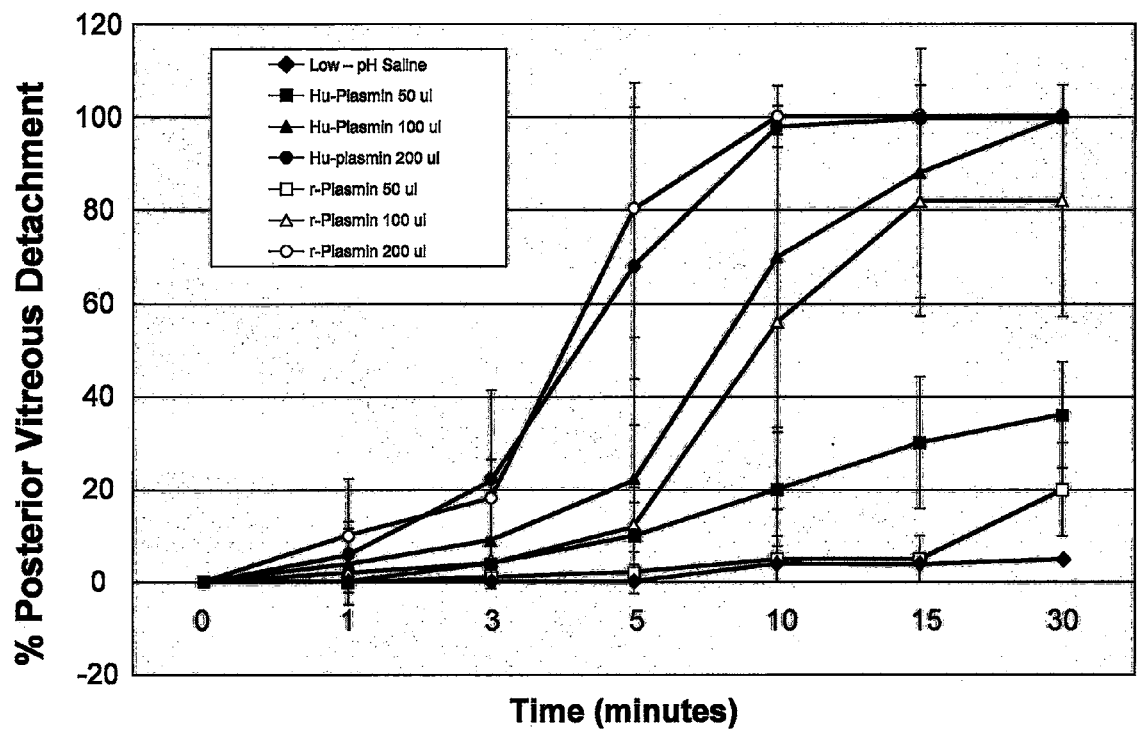
FIG. 15 shows a graphic representation of the extent of posterior vitreous detachment (PVD) versus time (minutes) after injection of eyes with the indicated volumes of h-plasmin (plasmin-derived human plasmin), r-plasmin (recombinant plasmin: r-plasmin is delta-plasmin), or saline.

At each time period after injection, the percent of PVD was determined on the ultrasound image. The mean and standard deviation at each time for each dose are depicted in FIG. 15. There were no significant differences in percent of PVD among doses of plasmin for times 0 and 1 minute after injection. At 3 minutes after injection, 200 µl h-plasmin (18.0±SD 8.4%) and 200 µl r-plasmin (22.0±SD 8.4%) had significantly higher percentages of PVD than the other concentrations ($P=0.0038$). At 5 minutes after injection, again, the 200 µl h-plasmin (80.0±SD 27.4%) and 200 µl r-plasmin (68.0±SD 34.2%) had significantly higher percentages of PVD than the other concentrations ($P<0.0001$). At 10 minutes after injection, the 200 µl h-plasmin (100.0±SD 0%) and 200 µl r-plasmin (98.0±SD 4.5%) were significantly greater than the 100 µl h-plasmin (56.0±SD 40.4%) and 100 µl r-plasmin (70.0±SD 36.7%), which were significantly greater than the 50 µl r- and h-plasmin and saline ($P<0.0001$). At 15 minutes, there were no significant differences between the 200 and 100 µl plasmin doses; however, these doses had % PVD that were significantly greater than the 50 µl plasmins and saline. The 50 µl r-plasmin (30.0±SD 14.1%) did have a significantly higher % PVD than the 50 µl h-plasmin (5.0±SD 5.0%) ($P=0.03$) at 15 minutes. At 30 minutes, the 200 and 100 µl plasmin doses had significantly higher % PVD than the 50 µl plasmin doses, which had significantly higher % PVD than the saline ($P<0.0001$) (FIG. 15).

Time to development the first evidence of PVD was also recorded for each dosage group (FIG. 16). There were no significant differences between time to first PVD among the 200 and 100 µl plasmin doses and the 50 µl r-plasmin dose, with means that ranged from 1.8 to 5.3 minutes. The 50 µl h-plasmin dose (mean 13.6 minutes) did have a significantly longer time to first PVD than the other dose groups other than the saline group (FIG. 16).

Time to 100% PVD was recorded for each dosage group (FIG. 17). There was no significant difference in the time to 100% PVD between the 200 µl plasmin doses (mean of 7 to 9 minutes). The 100 µl and 200 µl r-plasmin doses were also not significantly different. However the 100 µl h-plasmin did have a significantly longer duration to 100% PVD than the r-plasmin dose (FIG. 17 (+)). The 50 µl plasmin doses and the saline control were significantly lower than the other doses ($P<0.0001$).

In general, PVD occurred in a time and dose dependent manner. In the highest dose groups (200 µl), PVD began between 1 and 3 minutes after injection and achieved 100% PVD by 10 to 15 minutes. In the 100 µl dose groups, the time of PVD initiation to 100% PVD was consistently delayed compared to the 200 µl group. At most time periods, there were no significant differences within dose groups among the recombinant and human-derived plasmin. However, in the lower dose groups, the 50 µl h-plasmin did have a significantly lower % PVD than the 50 µl r-plasmin at 15 and 30 minutes after injection and the 50 µl h-plasmin dose did have a significantly longer time to first PVD than the 50 µl r-plasmin.

What is claimed is:

1. A method of liquefying a vitreous or a portion thereof, and/or inducing posterior vitreous detachment of an eye of a subject, comprising
    contacting the vitreous and/or the aqueous humor in the eye of the subject with an effective amount of a composition comprising:
        a polypeptide that is at least 95% identical to the sequence shown in SEQ ID NO: 2,
        wherein the polypeptide comprises an N-terminal kringle domain that binds to immobilized lysine and a C-terminal serine protease domain that has protease activity; and
    wherein the method results in liquefying the vitreous and/or inducing posterior vitreous detachment (PVD) of the eye of the subject.

2. The method of claim 1, wherein the polypeptide is the sequence shown in SEQ ID NO: 2.

3. The method of claim 1, wherein the polypeptide exhibits a fibrinolytic activity that is inhibited by α2-antiplasmin at a rate of inhibition that is at least about 5-fold faster than the rate of inhibition of the fibrinolytic activity of human mini-plasmin by α2-antiplasmin.

4. The method of claim 3, wherein the rate of inhibition is at least about 10-fold faster than the rate of inhibition of human mini-plasmin.

5. The method of claim 1, wherein the immobilized lysine is lysine bound to a solid support matrix selected from the group consisting of lysine-agarose, lysine-hydrogel, and lysine-cross-linked agarose.

6. The method of claim 5, wherein the immobilized lysine is lysine-cross-linked agarose.

7. The method of claim 1, wherein the polypeptide exhibits a lower binding affinity for fibrinogen than the binding affinity for fibrinogen of human mini-plasmin.

8. The method of claim 1, wherein the polypeptide exhibits higher binding affinity for partially cleaved fibrin than the binding affinity for partially cleaved fibrin of human mini-plasmin.

9. The method of claim 1, wherein the polypeptide has an arginine residue at a relative position analogous to that of position 76 of the amino acid sequence shown in SEQ ID NO: 2.

10. The method of claim 1, wherein the composition is a liquid solution, and wherein the contacting the vitreous and/or the aqueous humor with the composition comprises injecting the liquid solution into the vitreous and/or the aqueous humor of the eye of a subject.

11. The method of claim 1, wherein the effective amount of the composition is in the range of 0.005 mg to 1 mg.

12. The method of claim 1, wherein the subject has a vitreoretinal disease or disorder.

13. The method of claim 1, wherein the polypeptide is at least 95% identical to the sequence shown in SEQ ID NO: 2.

14. The method of claim 1, wherein the polypeptide is at least 98% identical to the sequence shown in SEQ ID NO: 2.

15. The method of claim 1, wherein the polypeptide is encoded by a nucleic acid having the nucleotide sequence of SEQ ID NO: 1 or a degenerate variant of SEQ ID NO: 1 that encodes SEQ ID NO: 2.

16. The method of claim 1, wherein the polypeptide can be activated by a plasminogen activator.

17. The method of claim 15, wherein the plasminogen activator is tissue plasminogen activator (tPA), urokinase, or streptokinase.

18. The method of claim 1, wherein the contacting comprises injecting the composition into the vitreous and/or aqueous humor in the eye of the subject.

19. The method of claim 1, wherein the method is performed as an adjunct to or an alternative of vitrectomy.

20. The method of claim 4, wherein the rate of inhibition is at least about 20-fold-faster than the rate of inhibition of human mini-plasmin.

21. The method of claim 20, wherein the rate of inhibition is at least about 30-fold-faster than the rate of inhibition of human mini-plasmin.

22. The method of claim 21, wherein the rate of inhibition is at least about 40-fold-faster than the rate of inhibition of human mini-plasmin.

* * * * *

SEQUENCE LISTING

```
<160> NUMBER OF SEQ ID NOS: 9

<210> SEQ ID NO 1
<211> LENGTH: 1008
<212> TYPE: DNA
<213> ORGANISM: Artificial Sequence
<220> FEATURE:
<223> OTHER INFORMATION: polynucletoide comprising a nucleotide sequence
      encoding a polypeptide having a single N-terminal kringle domain
      homoogous to a kringle domain of native human plasminogen

<400> SEQUENCE: 1
aaagtctatt tatctgaatg taaaacaggc aatggtaaaa actatcgcgg taccatgtcc        60
aaaacaaaaa acggtatcac ttgtcaaaaa tggtctagca cttcacccca tcgtcctcgt       120
```

```
ttctcccctg cgacccatcc ctctgaaggc ctcgaagaaa actactgccg caaccccgat    180
aatgatcctc aaggcccatg gtgttatact accgatcctg aaaaacgtta tgactattgc    240
gatatcttag aatgcgcagc cccttctttt gattgcggca aaccacaagt tgaacccaag    300
aaatgtccag gtcgtgttgt cggcggttgt gttgcgcatc cccacagttg gccgtggcag    360
gtctcattac gtaccggtt tggaatgcac ttttgtggcg gcactctcat ctcgcccgaa     420
tgggttctta cagctgcaca ctgtttggaa aaaagccccc gtccttcttc ttataaagtt    480
atcctcggcg cacatcaaga agtcaattta gaacctcatg tacaagaaat cgaagtatct    540
cgtttattcc tggaaccgac tcgcaaagac atcgcattac ttaaactgtc ctcccccgct    600
gtgatcaccg ataaagtaat tcccgcgtgt ttaccttctc ctaattatgt tgttgcagat    660
cgtacagaat gctttattac cggctggggt gaaactcaag gtacttttgg tgcgggactc    720
ctgaaagaag cacagttacc agtcatcgaa aacaaagtat gtaatcgcta cgaattctta    780
aacggtcgtg ttcaatccac agaattgtgc gcaggtcatt tagcaggtgg cactgatagc    840
tgtcaaggtg attcaggtgg tcctctcgta tgtttcgaaa aagataaata tattctgcaa    900
ggcgtcacct cttgggggttt aggttgtgct cgtcccaata aacctggtgt atatgtacgt    960
gtaagtcgtt ttgttacctg gattgaaggt gttatgcgga caaactaa                1008
```

<210> SEQ ID NO 2
<211> LENGTH: 335
<212> TYPE: PRT
<213> ORGANISM: Artificial Sequence
<220> FEATURE:
<223> OTHER INFORMATION: a polypeptide having a single N-terminal
kringle domain homoogous to a kringle domain of native human
plasminogen

<400> SEQUENCE: 2

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Ala Ala Pro Ser Phe Asp Cys Gly Lys Pro Gln
                85                  90                  95

Val Glu Pro Lys Lys Cys Pro Gly Arg Val Val Gly Gly Cys Val Ala
            100                 105                 110

His Pro His Ser Trp Pro Trp Gln Val Ser Leu Arg Thr Arg Phe Gly
        115                 120                 125

Met His Phe Cys Gly Gly Thr Leu Ile Ser Pro Glu Trp Val Leu Thr
    130                 135                 140

Ala Ala His Cys Leu Glu Lys Ser Pro Arg Pro Ser Ser Tyr Lys Val
145                 150                 155                 160

Ile Leu Gly Ala His Gln Glu Val Asn Leu Glu Pro His Val Gln Glu
                165                 170                 175

Ile Glu Val Ser Arg Leu Phe Leu Glu Pro Thr Arg Lys Asp Ile Ala
            180                 185                 190

Leu Leu Lys Leu Ser Ser Pro Ala Val Ile Thr Asp Lys Val Ile Pro

```
                195              200              205
Ala Cys Leu Pro Ser Pro Asn Tyr Val Val Ala Asp Arg Thr Glu Cys
    210              215              220

Phe Ile Thr Gly Trp Gly Glu Thr Gln Gly Thr Phe Gly Ala Gly Leu
225              230              235              240

Leu Lys Glu Ala Gln Leu Pro Val Ile Glu Asn Lys Val Cys Asn Arg
            245              250              255

Tyr Glu Phe Leu Asn Gly Arg Val Gln Ser Thr Glu Leu Cys Ala Gly
            260              265              270

His Leu Ala Gly Gly Thr Asp Ser Cys Gln Gly Asp Ser Gly Gly Pro
        275              280              285

Leu Val Cys Phe Glu Lys Asp Lys Tyr Ile Leu Gln Gly Val Thr Ser
    290              295              300

Trp Gly Leu Gly Cys Ala Arg Pro Asn Lys Pro Gly Val Tyr Val Arg
305              310              315              320

Val Ser Arg Phe Val Thr Trp Ile Glu Gly Val Met Arg Asn Asn
            325              330              335

<210> SEQ ID NO 3
<211> LENGTH: 2432
<212> TYPE: DNA
<213> ORGANISM: Homo sapiens
<220> FEATURE:
<221> NAME/KEY: misc_feature
<223> OTHER INFORMATION: Human plasminogen

<400> SEQUENCE: 3
atggaacata aggaagtggt tcttctactt cttttatttc tgaaatcagg tcaaggagag      60
cctctggatg actatgtgaa tacccagggg gcttcactgt tcagtgtcac taagaagcag     120
ctgggagcag aagtataga agaatgtgca gcaaaatgtg aggaggacga agaattcacc      180
tgcagggcat tccaatatca cagtaaagag caacaatgtg tgataatggc tgaaaacagg     240
aagtcctcca taatcattag gatgagagat gtagttttat ttgaaaagaa agtgtatctc     300
tcagagtgca agactgggaa tggaaagaac tacagaggga cgatgtccaa aacaaaaaat     360
ggcatcacct gtcaaaaatg gagttccact tctccccaca gacctagatt ctcacctgct     420
acacacccct cagagggact ggaggagaac tactgcagga atccagacaa cgatccgcag     480 gggcctggt gctatactac tgatccagaa aagagatatg actactgcga cattcttgag     540
tgtgaagagg aatgtatgca ttgcagtgga gaaaactatg acggcaaaat ttccaagacc     600
atgtctggac tggaatgcca ggcctgggac tctcagagcc cacacgctca tggatacatt     660
ccttccaaat ttccaaacaa gaacctgaag aagaattact gtcgtaaccc cgataggga      720 ctgcggcctt ggtgtttcac caccgacccc aacaagcgct gggaactttg cgacatcccc     780
cgctgcacaa cacctccacc atcttctggt cccacctacc agtgtctgaa gggaacaggt     840
gaaaactatc gcgggaatgt ggctgttacc gtttccgggc acacctgtca gcactggagt     900
gcacagaccc ctcacacaca taacaggaca ccagaaaact cccctgcaa aaatttggat     960 gaaaactact gccgcaatcc tgacggaaaa agggcccat ggtgccatac aaccaacagc    1020
caagtgcggt gggagtactg taagataccg tcctgtgact cctccccagt atccacggaa    1080
caattggctc ccacagcacc acctgagcta accctgtgg tccaggactg ctaccatggt    1140
gatggacaga gctaccgagg cacatcctcc accaccacca caggaaagaa gtgtcagtct    1200
tggtcatcta tgacaccaca ccggcaccag aagacccag aaaactaccc aaatgctggc    1260
ctgacaatga actactgcag gaatccagat gccgataaag cccctggtg ttttaccaca    1320
```

-continued

```
gaccccagcg tcaggtggga gtactgcaac ctgaaaaaat gctcaggaac agaagcgagt   1380
gttgtagcac ctccgcctgt tgtcctgctt ccagatgtag agactccttc cgaagaagac   1440
tgtatgtttg ggaatgggaa aggataccga ggcaagaggg cgaccactgt tactgggacg   1500
ccatgccagg actgggctgc ccaggagccc catagacaca gcattttcac tccagagaca   1560
aatccacggg cggtctggaa aaaaattac tgccgtaacc ctgatggtga tgtaggtggt   1620
ccctggtgct acacgacaaa tccaagaaaa ctttacgact actgtgatgt ccctcagtgt   1680
gcggcccctt catttgattg tgggaagcct caagtggagc cgaagaaatg tcctggaagg   1740
gttgtggggg ggtgtgtggc ccacccacat tcctggccct ggcaagtcag tcttagaaca   1800
aggtttggaa tgcacttctg tggaggcacc ttgatatccc cagagtgggt gttgactgct   1860
gcccactgct tggagaagtc cccaaggcct tcatcctaca aggtcatcct gggtgcacac   1920
caagaagtga atctcgaacc gcatgttcag gaaatagaag tgtctaggct gttcttggag   1980
cccacacgaa aagatattgc cttgctaaag ctaagcagtc ctgccgtcat cactgacaaa   2040
gtaatcccag cttgtctgcc atccccaaat tatgtggtcg ctgaccggac cgaatgtttc   2100
atcactggct ggggagaaac ccaaggtact tttggagctg gccttctcaa ggaagcccag   2160
ctccctgtga ttgagaataa agtgtgcaat cgctatgagt ttctgaatgg aagagtccaa   2220
tccaccgaac tctgtgctgg gcatttggcc ggaggcactg acagttgcca gggtgacagt   2280
ggaggtcctc tggtttgctt cgagaaggac aaatacattt tacaaggagt cacttcttgg   2340
ggtcttggct gtgcacgccc caataagcct ggtgtctatg ttcgtgtttc aaggtttgtt   2400
acttggattg agggagtgat gagaaataat ta                                 2432
```

<210> SEQ ID NO 4
<211> LENGTH: 810
<212> TYPE: PRT
<213> ORGANISM: Homo sapiens
<220> FEATURE:
<221> NAME/KEY: PEPTIDE
<222> LOCATION: (1)..(810)
<223> OTHER INFORMATION: Human plasminogen

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
        50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160
```

```
Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
            195                 200                 205

Trp Asp Ser Gln Ser Pro His Ala His Gly Tyr Ile Pro Ser Lys Phe
        210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
        370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
        530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
```

```
                      580                 585                 590
Pro Trp Gln Val Ser Leu Arg Thr Arg Phe Gly Met His Phe Cys Gly
            595                 600                 605
Gly Thr Leu Ile Ser Pro Glu Trp Val Leu Thr Ala Ala His Cys Leu
            610                 615                 620
Glu Lys Ser Pro Arg Pro Ser Ser Tyr Lys Val Ile Leu Gly Ala His
625                 630                 635                 640
Gln Glu Val Asn Leu Glu Pro His Val Gln Ile Glu Val Ser Arg
                645                 650                 655
Leu Phe Leu Glu Pro Thr Arg Lys Asp Ile Ala Leu Leu Lys Leu Ser
            660                 665                 670
Ser Pro Ala Val Ile Thr Asp Lys Val Ile Pro Ala Cys Leu Pro Ser
            675                 680                 685
Pro Asn Tyr Val Val Ala Asp Arg Thr Glu Cys Phe Ile Thr Gly Trp
            690                 695                 700
Gly Glu Thr Gln Gly Thr Phe Gly Ala Gly Leu Leu Lys Glu Ala Gln
705                 710                 715                 720
Leu Pro Val Ile Glu Asn Lys Val Cys Asn Arg Tyr Glu Phe Leu Asn
            725                 730                 735
Gly Arg Val Gln Ser Thr Glu Leu Cys Ala Gly His Leu Ala Gly Gly
            740                 745                 750
Thr Asp Ser Cys Gln Gly Asp Ser Gly Gly Pro Leu Val Cys Phe Glu
            755                 760                 765
Lys Asp Lys Tyr Ile Leu Gln Gly Val Thr Ser Trp Gly Leu Gly Cys
            770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
            805                 810

<210> SEQ ID NO 5
<211> LENGTH: 79
<212> TYPE: PRT
<213> ORGANISM: Artificial Sequence
<220> FEATURE:
<223> OTHER INFORMATION: kringle domain 1 of native human plasmin(ogen)

<400> SEQUENCE: 5

Cys Lys Thr Gly Asn Gly Lys Asn Tyr Arg Gly Thr Met Ser Lys Thr
1               5                   10                  15
Lys Asn Gly Ile Thr Cys Gln Lys Trp Ser Ser Thr Ser Pro His Arg
            20                  25                  30
Pro Arg Phe Ser Pro Ala Thr His Pro Ser Glu Gly Leu Glu Glu Asn
        35                  40                  45
Tyr Cys Arg Asn Pro Asp Asn Asp Pro Gln Gly Pro Trp Cys Tyr Thr
    50                  55                  60
Thr Asp Pro Glu Lys Arg Tyr Asp Tyr Cys Asp Ile Leu Glu Cys
65                  70                  75

<210> SEQ ID NO 6
<211> LENGTH: 78
<212> TYPE: PRT
<213> ORGANISM: Artificial Sequence
<220> FEATURE:
<223> OTHER INFORMATION: kringle domain 2 of native human plasmin(ogen)

<400> SEQUENCE: 6

Cys Met His Cys Ser Gly Glu Asn Tyr Asp Gly Lys Ile Ser Lys Thr
```

```
                1               5                  10                 15
Met Ser Gly Leu Glu Cys Gln Ala Trp Asp Ser Gln Ser Pro His Ala
                20                 25                 30

His Gly Tyr Ile Pro Ser Lys Phe Pro Asn Lys Asn Leu Lys Lys Asn
            35                 40                 45

Tyr Cys Arg Asn Pro Asp Arg Glu Leu Arg Pro Trp Cys Phe Thr Thr
        50                 55                 60

Asp Pro Asn Lys Arg Trp Glu Leu Cys Asp Ile Pro Arg Cys
65                  70                 75

<210> SEQ ID NO 7
<211> LENGTH: 78
<212> TYPE: PRT
<213> ORGANISM: Artificial Sequence
<220> FEATURE:
<223> OTHER INFORMATION: kringle domain 3 of native human plasmin(ogen)

<400> SEQUENCE: 7

Cys Leu Lys Gly Thr Gly Glu Asn Tyr Arg Gly Asn Val Ala Val Thr
1               5                  10                 15

Val Ser Gly His Thr Cys Gln His Trp Ser Ala Gln Thr Pro His Thr
                20                 25                 30

His Asn Arg Thr Pro Glu Asn Phe Pro Cys Lys Asn Leu Asp Glu Asn
            35                 40                 45

Tyr Cys Arg Asn Pro Asp Gly Lys Arg Ala Pro Trp Cys His Thr Thr
        50                 55                 60

Asn Ser Gln Val Arg Trp Glu Tyr Cys Lys Ile Pro Ser Cys
65                  70                 75

<210> SEQ ID NO 8
<211> LENGTH: 78
<212> TYPE: PRT
<213> ORGANISM: Artificial Sequence
<220> FEATURE:
<223> OTHER INFORMATION: kringle domain 4 of native human plasmin(ogen)

<400> SEQUENCE: 8

Cys Tyr His Gly Asp Gly Gln Ser Tyr Arg Gly Thr Ser Ser Thr Thr
1               5                  10                 15

Thr Thr Gly Lys Lys Cys Gln Ser Trp Ser Ser Met Thr Pro His Arg
                20                 25                 30

His Gln Lys Thr Pro Glu Asn Tyr Pro Asn Ala Gly Leu Thr Met Asn
            35                 40                 45

Tyr Cys Arg Asn Pro Asp Ala Asp Lys Gly Pro Trp Cys Phe Thr Thr
        50                 55                 60

Asp Pro Ser Val Arg Trp Glu Tyr Cys Asn Leu Lys Lys Cys
65                  70                 75

<210> SEQ ID NO 9
<211> LENGTH: 80
<212> TYPE: PRT
<213> ORGANISM: Artificial Sequence
<220> FEATURE:
<223> OTHER INFORMATION: kringle domain 5 of native human plasmin(ogen)

<400> SEQUENCE: 9

Cys Met Phe Gly Asn Gly Lys Gly Tyr Arg Gly Lys Arg Ala Thr Thr
1               5                  10                 15

Val Thr Gly Thr Pro Cys Gln Asp Trp Ala Ala Gln Glu Pro His Arg
                20                 25                 30
```

```
                                  -continued
His Ser Ile Phe Thr Pro Glu Thr Asn Pro Arg Ala Gly Leu Glu Lys
        35                  40                  45

Asn Tyr Cys Arg Asn Pro Asp Gly Asp Val Gly Gly Pro Trp Cys Tyr
    50                  55                  60

Thr Thr Asn Pro Arg Lys Leu Tyr Asp Tyr Cys Asp Val Pro Gln Cys
65                  70                  75                  80
```